United States Patent
Bader et al.

(10) Patent No.: US 11,337,909 B2
(45) Date of Patent: May 24, 2022

(54) METHODS FOR MODULATING PIGMENTATION BY ANGIOTENSIN-CONVERTING ENZYME 2 MODULATION

(71) Applicant: Max-Delbrück-Centrum für Molekulare Medizin in der Helmholtz-Gemeinschaft, Berlin (DE)

(72) Inventors: Michael Bader, Berlin (DE); Fatimunnisa Qadri, Berlin (DE); Mihail Todiras, Berlin (DE); Natalia Alenina, Berlin (DE)

(73) Assignee: MAX-DELBRÜCK-CENTRUM FÜR MOLEKULARE MEDIZIN IN DER HELMHOLTZ-GEMEINSCHAFT, Berlin (DE)

( * ) Notice: Subject to any disclaimer, the term of this patent is extended or adjusted under 35 U.S.C. 154(b) by 15 days.

(21) Appl. No.: 16/768,028

(22) PCT Filed: Nov. 29, 2018

(86) PCT No.: PCT/EP2018/082997
§ 371 (c)(1),
(2) Date: May 28, 2020

(87) PCT Pub. No.: WO2019/106085
PCT Pub. Date: Jun. 6, 2019

(65) Prior Publication Data
US 2020/0360258 A1 Nov. 19, 2020

(30) Foreign Application Priority Data
Nov. 29, 2017 (EP) .................................. 17204424

(51) Int. Cl.
| | | |
|---|---|---|
| *A61K 8/49* | (2006.01) |
| *A61K 8/41* | (2006.01) |
| *A61Q 5/08* | (2006.01) |
| *A61Q 5/10* | (2006.01) |
| *A61Q 17/04* | (2006.01) |
| *A61Q 19/02* | (2006.01) |
| *A61Q 19/04* | (2006.01) |
| *A61K 9/00* | (2006.01) |
| *A61K 31/4174* | (2006.01) |
| *A61K 45/06* | (2006.01) |
| *A61K 8/64* | (2006.01) |
| *A61Q 19/00* | (2006.01) |
| *A61P 17/00* | (2006.01) |
| *A61K 8/35* | (2006.01) |
| *A61K 8/40* | (2006.01) |
| *A61K 9/70* | (2006.01) |
| *A61K 31/655* | (2006.01) |
| *A61K 38/34* | (2006.01) |
| *A61P 35/00* | (2006.01) |
| *C12N 9/48* | (2006.01) |

(52) U.S. Cl.
CPC ............ *A61K 8/4946* (2013.01); *A61K 8/411* (2013.01); *A61Q 5/08* (2013.01); *A61Q 5/10* (2013.01); *A61Q 17/04* (2013.01); *A61Q 19/02* (2013.01); *A61Q 19/04* (2013.01)

(58) Field of Classification Search
CPC ............ A61K 2300/00; A61K 31/4174; A61K 31/655; A61K 2800/78; A61K 2800/782; A61K 38/34; A61K 45/06; A61K 8/35; A61K 8/40; A61K 8/411; A61K 8/4946; A61K 8/64; A61K 9/0014; A61K 9/70; A61P 17/00; A61P 35/00; A61Q 17/04; A61Q 19/00; A61Q 19/004; A61Q 19/02; A61Q 19/04; A61Q 5/08; A61Q 5/10; C12N 9/485; C12Y 304/17023
See application file for complete search history.

(56) References Cited

U.S. PATENT DOCUMENTS

| | | |
|---|---|---|
| 8,946,162 B2 | 2/2015 | Janzek-Hawlat et al. |
| 2004/0082496 A1 | 4/2004 | Acton et al. |
| 2010/0204286 A1 | 8/2010 | Donahue et al. |

FOREIGN PATENT DOCUMENTS

| | | |
|---|---|---|
| AT | 506 632 A1 | 10/2009 |
| WO | WO 02/39997 A2 | 5/2002 |
| WO | WO 2005/072696 A1 | 8/2005 |
| WO | WO 2008/066770 A2 | 6/2008 |

OTHER PUBLICATIONS

Byrnes et al.; "Effects of the ACE2 inhibitor GL1001 on acute dextran sodium sulfate-induced colitis in mice"; Inflamm. Res.; (2009) 58: 819-827. Published online Jun. 11, 2009.*

Rawlings et al.; Clarke et al.; "Angiotensin-converting enzyme 2"; Handbook of Proteolytic Enzymes, Ch. 100; pp. 499-504. Published Oct. 30, 2012.*

Liu et al.; "Angiotensin II stimulates melanogenesis via the protein kinase C pathway"; Experimental and Therapeutic Medicine; 10: 1528-1532. Published 2015.*

(Continued)

*Primary Examiner* — Jeffrey T. Palenik
(74) *Attorney, Agent, or Firm* — Knobbe, Martens, Olson & Bear, LLP

(57) ABSTRACT

A cosmetic method for modulating pigmentation in a subject includes administering a modulator of angiotensin-converting enzyme 2 (ACE2 modulator) to the subject. The ACE2 modulator can be an inhibitor of angiotensin-converting enzyme 2 (ACE2 inhibitor), in which case, the ACE2 inhibitor can be administered to increase pigmentation in the subject. The ACE2 modulator can also be an activator of angiotensin-converting enzyme 2 (ACE2 activator), in which case the ACE2 activator can be administered to decrease pigmentation in the subject. The treatment of inflammatory skin disease can also be achieved by inhibition of angiotensin-converting enzyme 2.

Figure 1:
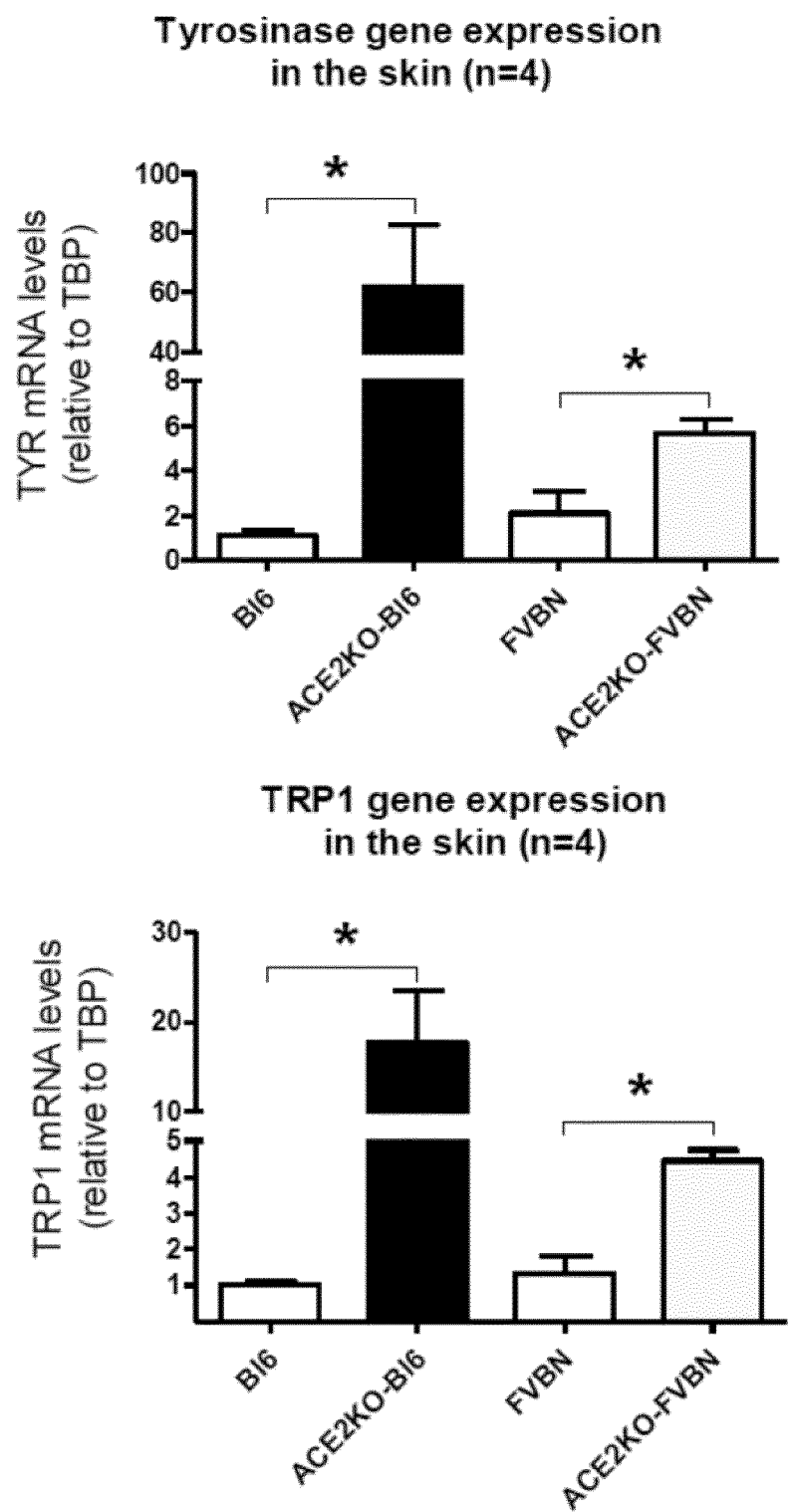
Figure 1:
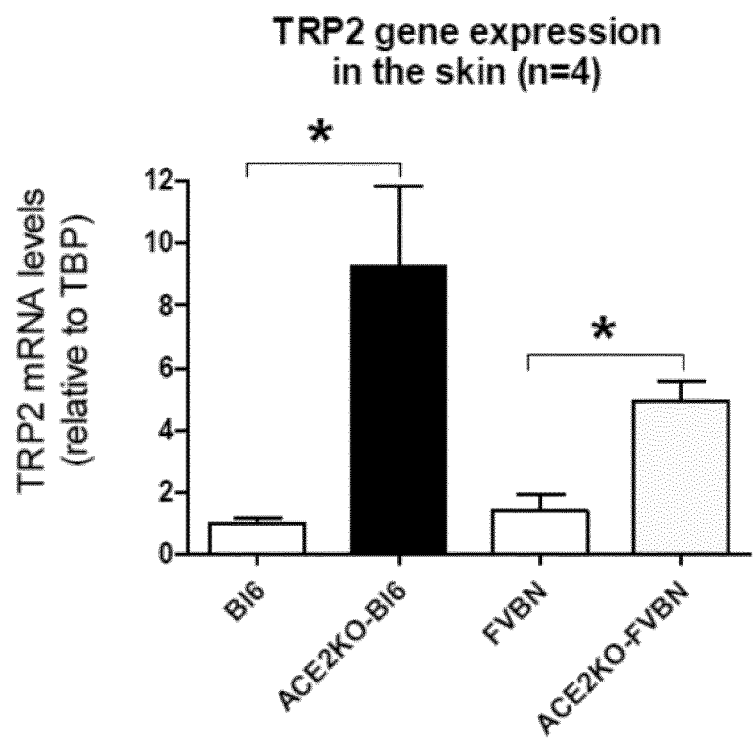
Figure 1:
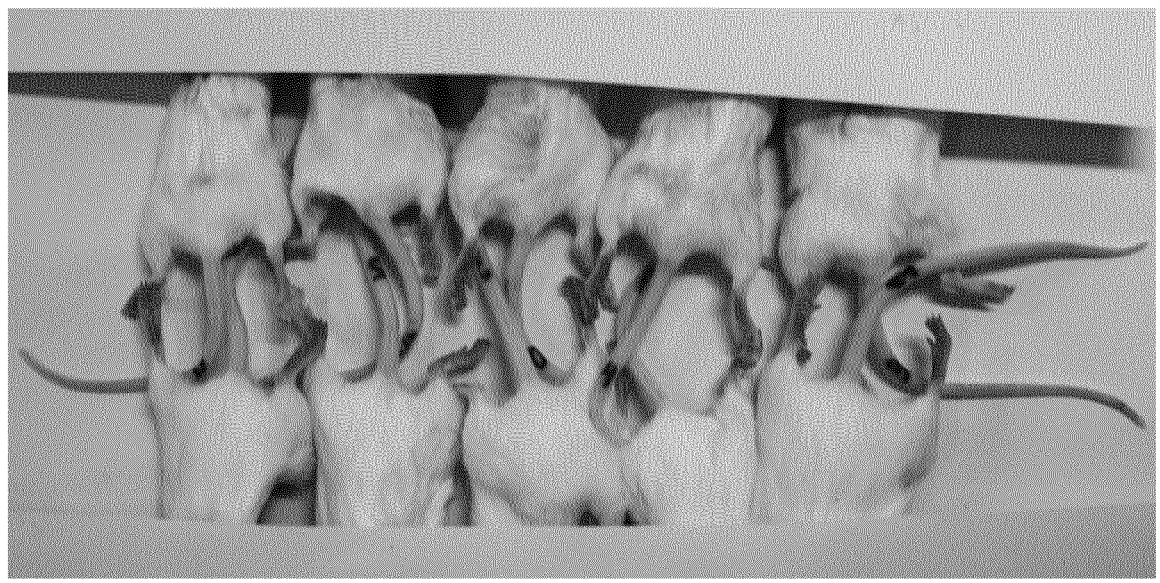

8 Claims, 7 Drawing Sheets
Specification includes a Sequence Listing.

(56) References Cited

OTHER PUBLICATIONS

International Search Report and Written Opinion, PCT/EP2018/082997, dated Mar. 14, 2019.
Tao, et al., 2016 "Angiotensin-converting enzyme 2 activator diminazine aceturate prevents lipopolysaccharide-induced inflammation by inhibiting MAPK and NF-κB pathways in human retinal pigment epithelium", Journal of Neuroinflammation, vol. 13 (in 21 pages).

* cited by examiner

Melanin in human abdominal skin in vitro

METHODS FOR MODULATING PIGMENTATION BY ANGIOTENSIN-CONVERTING ENZYME 2 MODULATION

REFERENCE TO SEQUENCE LISTING

The present application is being filed along with a Sequence Listing in electronic format. The Sequence Listing is provided as a file entitled 32891622_1_1.TXT, created May 28, 2020, which is 7.20 Kb in size. The information in the electronic format of the Sequence Listing is incorporated herein by reference in its entirety.

DESCRIPTION

The invention relates to a cosmetic method for modulating pigmentation in a subject, comprising administering a modulator of angiotensin-converting enzyme 2 (ACE2 modulator) to said subject. The invention encompasses methods in which the ACE2 modulator is an inhibitor of angiotensin-converting enzyme 2 (ACE2 inhibitor) and the ACE2 inhibitor is administered to increase pigmentation in said subject, in addition to methods where the ACE2 modulator is an activator of angiotensin-converting enzyme 2 (ACE2 activator) and the ACE2 activator is administered to decrease pigmentation in said subject. The invention further relates to the treatment of inflammatory skin disease by inhibition of angiotensin-converting enzyme 2. In some embodiments, the method relates to an inhibitor of angiotensin-converting enzyme 2 (ACE2 inhibitor) for use as a medicament in the treatment of inflammatory skin disease. The invention further relates to corresponding pharmaceutical and cosmetic compositions, preferably suited for topical administration of an ACE2 modulator.

BACKGROUND

Skin whitening, or skin lightening, is widespread internationally and is often considered as the procedure of using cosmetic products and/or pharmacological agents to lighten the skin tone, or provide an even skin complexion, for example by reducing the melanin content and/or production in the skin. The global skin lightening products market is considered to be undergoing significant growth with the growing consciousness among people regarding their appearance and skin tone. According to some reports, such as a Research Report by Future Market Insights, estimates that the global skin lightening products market is expected to reach a valuation of over 24 Billion USD by the end of 2027. Modification of melanin content and/or production in the hair of a subject also represents a further cosmetic field of significant importance.

Furthermore, hyperpigmentation can be caused by sun damage, inflammation, or other skin injuries, including those related to acne vulgaris. People with darker skin tones are more prone to hyperpigmentation, especially with excess sun exposure. Melasma is also a common skin problem causing dark discolored patchy hyperpigmentation, often in pregnant women.

Inflammatory skin diseases such as protoporphyria, psoriasis, vitiligo, and others, as well as sunburns, are major medical and cosmetic problems with limited therapeutic options. Moreover, skin inflammation is the most important risk factor for formation of melanoma, a cancer with high mortality rates and few therapeutic options.

The α-melanocyte stimulating hormone (α-MSH) counteracts inflammatory skin diseases and protects from melanoma formation by acting on the melanocortin 1 receptor (MC1R) on different skin cells, including melanocytes and hair follicles. However, the therapeutic opportunity offered by the activation of the α-MSH/MC1R system has not yet been sufficiently exploited.

α-MSH is a 13-amino-acid peptide hormone generated by posttranslational processing from the precursor protein proopiomelanocortin (Ericson et al., 2017). Originally, it was discovered to be produced in the pituitary and named after its effects on pigmentation. However, α-MSH can be detected in numerous cell types also in the skin such as in melanocytes, keratinocytes, epithelial cells, B cells, natural killer cells, and subsets of T cells.

Its most obvious function in the skin is the stimulation of melanogenesis by activating the MC1R on melanocytes, thereby eliciting an increase in pigmentation of skin and hair. However, recent studies revealed that α-MSH also interacts with immune cells, and exerts antimicrobial, anti-inflammatory, and immunomodulatory activities. Activation of the MC1R, either by the natural ligand α-MSH or by synthetic substances, therefore became of therapeutic interest for the protection against inflammatory skin diseases induced by ultraviolet (UV) light or other noxes, such as psoriasis, acne, vitiligo, protoporphyria and others (Shah et al., 2016; Minder et al., 2017).

Since skin inflammation and UV-irradiation are also major risk factors for melanoma formation, MC1R agonists and α-MSH exerting genoprotective and antioxidant actions are promising targets for the prevention of melanoma formation (Abdel-Malek et al., 2014). Thus, activation of the α-MSH/MC1R system in the skin is of highest therapeutic value and several MC1R agonists have been developed for this purpose.

However, all these substances are peptides which have to be injected or implanted to reach the MC1R, which renders them poorly suitable for most therapeutic indications. Besides activating the receptor of a peptide, one may also stabilize the peptide itself by inhibiting degrading proteases in order to boost its effects. This pharmacologic principle has already been several times successfully exploited, e.g., Gliptins inhibit DPPIV which degrades the hypoglycemic peptide, GLP-1 (Cahn et al., 2016), and ARNIs inhibit NEP, the enzyme degrading the antihypertensive natriuretic peptides (Campbell 2017). Also for α-MSH such a therapeutic approach is currently being evaluated, albeit in the hypothalamus. There the peptide interacts with MC4 receptors and exerts anorexigenic actions. In the hypo-thalamus α-MSH1-13 is degraded to α-MSH1-12 by prolylcarboxypeptidase (PRCP) (Wallingford et al., 2009).

The inventors and others have previously shown that PRCP-knockout (KO) mice are leaner than controls and stay slimmer when fed with a high-fed diet (Wallingford et al., 2009, Maier et al., 2017). Therefore, PRCP inhibitors, which should stabilize α-MSH, have been developed as anti-obesity drugs (Jeong & Diano, 2013). However, it was previously unknown which enzyme degrades α-MSH in the skin. Thus, a therapy based on stabilization of the peptide is not yet available for skin diseases or for modulation of pigmentation.

Enzyme inhibitors, in contrast to MC1R agonists, preferably in the form of small molecules, can penetrate the outer layers of the skin and may therefore be applied topically. Moreover, since α-MSH is the most important melanogenic factor, such substances may also be suitable for cosmetic purposes inducing tanning and preventing hair greying (Paus 2011).

The most effective substance stimulating the MC1R is Afamelatonide (NDP-MSH, melanotan I), a peptide in which several amino acids have been exchanged compared to α-MSH. It has an even higher activity than α-MSH on MC1R and has been successfully used in patients with several skin diseases, such as vitiligo, acne, and protoporphyria with only mild adverse effects (Minder et al., 2017).

Several additional peptidic MC1R agonists are being developed by different companies (Ericson et al., 2016). However, these substances are not specific for MC1R and need to be injected or applied in small subcutaneous implants, which drastically limits their applicability (Biba 2014). Only one specific small molecule MC1R agonist has been reported, BMS 470539 (Herpin et al., 2003), but it has only been tested in systemic inflammation models and not in the skin (Kang et al., 2006; Lindskog Jonsson et al., 2014).

ACE2 inhibitors have been previously developed, for example by Millenium Pharmaceuticals, Inc. (Takeda Pharmaceuticals, Cambridge, Mass.), but they were developed and disclosed for other medical indications (US 20040082496 A1, U.S. Pat. No. 6,632,830 B1), and Dyax (now Shire, Huang et al., 2003, not patented) developed molecules for use as centrally acting antiobesity and antihypertensive drugs.

ACE2 activators have been previously developed, for example Hernandez Prada et al (Hypertension 2008; 51:1312-1317) disclose Small-Molecule Angiotensin-Converting Enzyme 2 Activators xanthenone and resorcinolnaphthalein that enhance ACE2 activity in a dose-dependent manner and may be suitable for treating cardiovascular disease, hypertension or lung injury (WO 2008/066770). Kulemina and Ostrov describe further numerous ACE2 activators (Journal of Biomolecular Screening 2011; 16:878-885), and Shenoy et al (Am J Respir Crit Care Med Vol 187, Iss. 6, pp 648-657, Mar. 15, 2013) describe an antitrypanosomal drug, diminazene aceturate (DIZE), to enhance the enzymatic activity of ACE2 in vitro and in vivo. ACE2 peptides or variants thereof are also known to enhance ACE2 activity (EP 2332582, WO 2018/140456).

As such, the fields of cosmetics for modulating pigmentation of the hair and/or skin (increasing or decreasing pigmentation) and inflammatory skin disease are in significant need of agents that may be employed in treating and/or reducing the risk of inflammatory skin disease and/or modulating (increasing or decreasing) pigmentation in the skin and/or hair.

SUMMARY OF THE INVENTION

In light of the prior art the technical problem underlying the present invention is to provide alternative and/or improved means for modulating pigmentation. In some aspects, the problem underlying the invention is the provision of means for reducing pigmentation, thereby lightening hair and/or skin. In some aspects, the problem underlying the invention is the provision of means for increasing pigmentation, thereby darkening hair and/or skin. In some aspects, the problem underlying the invention is the provision of means for treating skin inflammation.

This problem is solved by the features of the independent claims. Preferred embodiments of the present invention are provided by the dependent claims.

The inventors have identified that angiotensin-converting enzyme 2 (ACE2) degrades α-MSH in the skin. This discovery represents the first identification of a functional relationship between ACE2 and α-MSH. ACE2 modulation is therefore a valuable mode of modulating pigmentation in cosmetic or therapeutic settings. ACE2-activation represents a valid approach towards cosmetic applications of skin lightening. ACE2-inhibition represents a valid therapeutic approach for the treatment of inflammatory skin diseases, UV-protection, prevention of melanoma, and for cosmetic applications, such as tanning and prevention of hair greying, by stabilization of α-MSH.

The various aspects of ACE2 modulation, either inhibition or activation, either cosmetic or therapeutic, are linked by unifying concept of the functional relationship between angiotensin-converting enzyme 2 (ACE2) activity, α-MSH and pigmentation. The relationship between these factors in the modulation of pigmentation, preferably of the skin or hair, represents a novel and unexpected finding of the present invention, suitable for distinguishing the present invention from the prior art and unifying the various aspects of the invention disclosed herein.

In one aspect, the invention therefore relates to a cosmetic method for modulating pigmentation in a subject, comprising administering a modulator of angiotensin-converting enzyme 2 (ACE2 modulator) to said subject.

ACE2 Inhibition

In one aspect, the invention therefore relates to a cosmetic method as described herein, wherein the ACE2 modulator is an inhibitor of angiotensin-converting enzyme 2 (ACE2 inhibitor) and the ACE2 inhibitor is administered to increase pigmentation in said subject.

As shown in the examples below, the ACE2 naturally limits the activity of α-MSH, thereby regulating melanin production. As such, the inhibition of the carboxypeptidase function of ACE2 leads either directly and/or indirectly to a larger amount of α-MSH and correspondingly higher levels of melanin in the subject.

In one embodiment, with respect to the cosmetic method, the ACE2 inhibitor inhibits the carboxypeptidase digestion of α-melanocyte stimulating hormone (α-MSH).

In one embodiment, with respect to the cosmetic method, the ACE2 inhibitor leads to elevated levels of α-MSH1-13 in subjects who have received ACE2 inhibitor treatment compared to subjects who have not received said treatment.

In some embodiments, the effect of ACE2 on α-melanocyte stimulating hormone (α-MSH), and in particular on α-MSH1-13, may be mediated directly or indirectly. For example, ACE2 may either directly or indirectly lead to degradation of α-MSH. Therefore, the use of an ACE2 inhibitor may lead directly to decreased ACE2 activity, which acts directly on α-MSH to a reduced extent. In other embodiments, the ACE2 inhibitor may lead to reduced ACE2 activity, which acts on one or more other agents, that in turn lead to reduced α-MSH degradation.

In one embodiment, with respect to the cosmetic method, the ACE2 inhibitor leads to elevated levels of one or more melanins in subjects who have received ACE2 inhibitor treatment compared to subjects who have not received said treatment.

Melanin is a term for a group of natural pigments found in most organisms. Melanin is produced by the oxidation of the amino acid tyrosine, followed by polymerization. The melanin pigments are produced in a specialized group of cells known as melanocytes. There are three basic types of melanin: eumelanin, pheomelanin, and neuromelanin. The most common type is eumelanin, of which there are two types—brown eumelanin and black eumelanin. Pheomelanin is a cysteine that contains red polymer of benzothiazine units largely responsible for red hair, among other pigmentation. In the human skin, melanogenesis is initiated by exposure to UV radiation, causing the skin to turn tan. Melanin is an effective absorbent of light; the pigment is able to dissipate over 99.9% of absorbed UV radiation. Because of this property, melanin is thought to protect skin cells from UVB radiation damage, reducing the risk of cancer, and it's considered that exposure to UV radiation is associated with increased risk of malignant melanoma, a cancer of the melanocytes cells. Studies have shown a lower incidence for skin cancer in individuals with more concentrated melanin, i.e. darker skin tone.

In some embodiments, with respect to the cosmetic method, the ACE2 inhibitor leads to elevated expression of one or more melanogenic genes, such a tyrosinase, Trp1, Trp2 and/or GPNMB, in subjects who have received ACE2 inhibitor treatment compared to subjects who have not received said treatment.

Such genes involved in melanogenesis may be determined by one skilled in the art. The desired effect of enabling greater melanogenesis is one advantage of the present invention. Essentially, any downstream effect of α-MSH may be enhanced by the present invention, which leads to greater levels of melanins in the subject.

In some embodiments, with respect to the cosmetic method, the elevated levels of α-MSH1-13, elevated levels of one or more melanins and/or elevated expression of one or more melanogenic genes occurs in the skin of a subject. This desired effect is particularly beneficial for topical administration of the ACE2 inhibitors, but may also arise after systemic administration of the inhibitor.

In some embodiments, with respect to the cosmetic method, the elevated levels of α-MSH1-13, elevated levels of one or more melanins and/or elevated expression of one or more melanogenic genes occurs in the hair follicle and/or hair of a subject. Topical and/or systemic administration may be employed to achieve this effect. In some embodiments, with respect to the cosmetic method, the ACE2 inhibitor is administered to said subject to prevent a loss of pigmentation in the hair, for example by reducing, preventing, reversing or reducing the likelihood of graying or whitening of hair.

This use may preferably be applied via topical administration to the scalp of a subject, but may also be obtained using systemic or other forms of administration. In some embodiments, with respect to the cosmetic method, the ACE2 inhibitor is administered topically. Topical administration may also involve hair creams, wax, hair spray, shampoo, or other hair care products.

ACE2 Activation

In one aspect, the invention therefore relates to a cosmetic method as described herein, wherein the ACE2 modulator is an activator of angiotensin-converting enzyme 2 (ACE2 activator) and the ACE2 activator is administered to decrease pigmentation in said subject.

In one embodiment of the cosmetic method, the ACE2 activator promotes carboxypeptidase digestion of α-melanocyte stimulating hormone (α-MSH).

In one embodiment of the cosmetic method, the ACE2 activator leads to reduced levels of α-MSH1-13 in subjects who have received ACE2 activator treatment compared to subjects who have not received said treatment.

In some embodiments, the effect of ACE2 on α-melanocyte stimulating hormone (α-MSH), and in particular on α-MSH1-13, may be mediated directly or indirectly. For example, ACE2 may either directly or indirectly lead to degradation of α-MSH. Therefore, the use of an ACE2 activator may lead directly to increased ACE2 activity which acts directly on α-MSH. In other embodiments, the ACE2 activator may lead to increased ACE2 activity, which acts on one or more other agents, than in turn lead to α-MSH degradation.

In one embodiment of the cosmetic method, the ACE2 activator leads to reduced levels of one or more melanins in subjects who have received ACE2 activator treatment compared to subjects who have not received said treatment.

In one embodiment of the cosmetic method, the ACE2 activator leads to reduced expression of one or more melanogenic genes, such a tyrosinase, Trp1, Trp2 and/or GPNMB, in subjects who have received ACE2 activator treatment compared to subjects who have not received said treatment.

In one embodiment of the cosmetic method, the reduced levels of α-MSH1-13, reduced levels of one or more melanins and/or reduced expression of one or more melanogenic genes occurs in the skin, hair follicle and/or hair of a subject.

In one embodiment of the cosmetic method, the ACE2 activator is administered to said subject to promote a lightening of hair color (bleaching).

In one embodiment of the cosmetic method, the pigmentation is decreased in the skin of the subject.

In one embodiment of the cosmetic method, the pigmentation is decreased in a hair follicle and/or the hair of the subject.

In one embodiment of the cosmetic method, the ACE2 activator is administered topically.

In some embodiments relating to decreasing pigmentation, the method is employed to address, manage, reduce, prevent, reverse or otherwise treat hyperpigmentation or unwanted pigmentation.

Hyperpigmentation can be caused by sun damage, inflammation, or other skin injuries, including those related to acne vulgaris. People with darker skin tones are more prone to hyperpigmentation, especially with excess sun exposure. Many forms of hyperpigmentation are caused by an excess production of melanin and are therefore responsive to the methods described herein regulating ACE2, alpha-MSH and accordingly melanin production. Hyperpigmentation can be diffuse or focal, affecting such areas as the face and the back of the hands. As the body ages, melanocyte distribution becomes less diffuse and its regulation less controlled by the body. UV light stimulates melanocyte activity, and where concentration of the cells is greater, hyperpigmentation occurs. Another form of hyperpigmentation is post inflammatory hyperpigmentation. These are dark and discoloured spots that appear on the skin following acne that has healed.

In some embodiments, the invention may be employed to address, manage, reduce, prevent, reverse or otherwise treat Melasma, also known as the "mask of pregnancy". Melasma is a common skin problem that causes dark discolored patchy hyperpigmentation. The patches are darker than usual skin color. It typically occurs on the face and is symmetrical, with matching marks on both sides of the face, caused by increased melanin production.

According to the present invention, the claims directed to the cosmetic methods clearly embody a method of treating the human body for cosmetic purposes but not for the therapeutic application, which is also possible. The claims directed to the cosmetic methods clearly cover a method of cosmetic use and are not necessarily related to the therapy of a human or animal body in the ordinary medical sense. The fact that a chemical product has both a cosmetic and a therapeutic effect when used to treat the human or animal body does not lead to inherent confusion between the two uses, and these two aspects are not inseparably linked.

The election of the subject to receive the administration enables separation of the clinical/medical and cosmetic uses. The one patient group comprises patients known to have inflammatory skin disease, whereas the second group comprises healthy persons who would receive no therapeutic benefit from the treatment. Moreover, the times necessary for appreciating the different effects may in some embodiments be so different that no unwanted overlap of the treatment would occur. Moreover, the preventative use of the ACE2 inhibitors as described herein can be determined from the cosmetic use by the term and duration of the treatment, in addition to the fact that particular individuals may clearly opt to employ the cosmetic use, for increasing pigmentation in the skin or hair, whereas others may employ it as a preventative measure to spend more time exposed out of doors. As such, these uses may differ in the modes of administration, duration of treatment and effects on skin pigmentation.

Compositions:

In a further aspect of the invention, a cosmetic composition is provided for modulating pigmentation in a subject comprising an ACE2 modulator and one or more acceptable carriers in a form suitable for topical administration. To the knowledge of the inventors, topical administration, preferably to the skin and/or hair, has not been previously described for ACE2-Modulator compositions. Previous reports on ACE2 modulators relate primarily to treating cardiac conditions, and are described for systemic administration. The topical administration of an ACE2 modulator, and in particular compositions for the topical administration comprising an ACE2 modulator, represent novel and unexpected aspects of the invention stemming from the identification by the inventors of the functional relationship between ACE2 and alpha MSH.

In one embodiment, the cosmetic composition is administered to increase pigmentation in a subject and the ACE2 modulator is an ACE2 inhibitor.

In one embodiment, the cosmetic composition comprises additionally one or more additional pigmentation enhancing agents, such as α-MSH or synthetic α-MSH analogues.

In one embodiment, the cosmetic composition is administered to decrease pigmentation in a subject and the ACE2 modulator is an ACE2 activator.

In one embodiment, the cosmetic composition comprises additionally one or more additional pigmentation reducing agents, such as hydroquinone, azelaic acid, koijic acid, niacinamide and/or cysteamine hydrochloride.

ACE2 Inhibitors for Use as a Medicament in the Treatment of Inflammatory Skin Disease:

In a further aspect, the invention relates to an inhibitor of angiotensin-converting enzyme 2 (ACE2 inhibitor) for use as a medicament in the treatment of inflammatory skin disease, and to methods for the treatment and/or prevention of various medical conditions considered to be "inflammatory skin disease". Despite a number of diseases being known to be inflammatory skin diseases, such as those described in more detail below, a skilled person is capable of detecting inflammation in the skin using standard techniques, for example by determining elevated levels of molecular markers, or by inspection of the akin and determining the presence of redness, swelling, painful areas or other markers of inflammation.

In some embodiments of the therapeutic use of an ACE2 inhibitor, the ACE2 inhibitor inhibits the carboxypeptidase digestion of α-melanocyte stimulating hormone (α-MSH).

In some embodiments of the therapeutic use of an ACE2 inhibitor, the ACE2 inhibitor leads to elevated levels of α-MSH1-13 in subjects who have received ACE2 inhibitor treatment compared to subjects who have not received said treatment.

In some embodiments of the therapeutic use of an ACE2 inhibitor, the ACE2 inhibitor leads to elevated levels of one or more melanins in subjects who have received ACE2 inhibitor treatment compared to subjects who have not received said treatment.

In some embodiments of the therapeutic use of an ACE2 inhibitor, the ACE2 inhibitor leads to elevated expression of one or more melanogenic genes, such a tyrosinase, Trp1, Trp2 and/or GPNMB, in subjects who have received ACE2 inhibitor treatment compared to subjects who have not received said treatment.

In some embodiments of the therapeutic use of an ACE2 inhibitor, the elevated levels of α-MSH1-13, elevated levels of one or more melanins and/or elevated expression of one or more melanogenic genes occurs in the skin of a subject.

Not to be limited by the above, α-MSH also interacts with immune cells, and exerts antimicrobial, anti-inflammatory, and immunomodulatory activities, in some cases independently of its effect in modulating melanin levels in a subject. Alpha-MSH can therefore itself potentially without an effect on melanin lead to an anti-inflammatory effect. In such embodiments, medical conditions involving inflammation of the skin, which are not related primarily to melanin synthesis or activity, may also be addressed by the present invention, due to the multiple roles of α-MSH.

In some embodiments, the inflammatory skin disease is protoporphyria, such as erythropoietic protoporphyria (EPP).

Erythropoietic protoporphyria (EPP) is a form of porphyria, which varies in severity and can be very painful. It arises from a deficiency in the enzyme ferrochelatase, leading to abnormally high levels of protoporphyrin in the erythrocytes, plasma, skin and liver. The severity varies significantly from individual to individual. EPP usually presents in childhood with the most common mode of presentation as acute photosensitivity of the skin. It affects areas exposed to the sun and tends to be intractable. A few minutes of exposure to the sun induces pruritus, erythema, swelling and pain. Longer periods of exposure may induce second degree burns.

In some embodiments, the inflammatory skin disease is psoriasis.

Psoriasis is an immune-mediated disease that causes raised, red, scaly patches to appear on the skin. It typically affects the outside of the elbows, knees or scalp, though it can appear on any location. Some people report that psoriasis is itchy, burns and stings.

In some embodiments, the inflammatory skin disease is vitiligo.

Vitiligo is a disease in which the pigment cells of the skin, melanocytes, are destroyed in certain areas. Symptoms and signs of vitiligo include loss of skin color in the form of depigmented, or white, patches of skin in any location on the body.

In some embodiments, the inflammatory skin disease is acne.

Acne is an irritating skin condition caused by trapped oil and debris on your skin. When facial pores become clogged with oil, bacteria on the face of a subject leads to acne breakouts. Acne can quickly become inflamed, causing painful, large red bumps on your skin.

In some embodiments, the inflammatory skin disease is solar urticaria (SU).

SU is a condition in which exposure to ultraviolet or UV radiation, or sometimes even visible light, induces a case of urticaria or hives that can appear in both covered and uncovered areas of the skin.

In some embodiments, the inflammatory skin disease is Hailey-Hailey disease.

Hailey-Hailey disease, or familial benign chronic pemphigus or familial benign pemphigus, is a genetic disorder that causes blisters to form on the skin. It is characterized by outbreaks of rashes and blisters in the skin, usually in the folds of the skins, but also often over large areas of the body.

In some embodiments, the inflammatory skin disease is Polymorphous light eruption (PLE)

Polymorphous light eruption (PLE), or polymorphic light eruption (PMLE), is a skin condition triggered by sunlight. Symptoms include skin irritations, which may be itchy or painful, and are sometimes confused with hives. These irritations appear upon or shortly after exposure to sunlight, and may last from 1 to 7 days.

In some embodiments, the inflammatory skin disease is alopecia areata.

Alopecia areata, also known as spot baldness, is a condition in which hair is lost from some or all areas of the body. Often it results in a few bald spots on the scalp, each about the size of a coin. Psychological stress may result. People are generally otherwise healthy. In a few, all the hair on the scalp or all body hair is lost and loss can be permanent. Alopecia areata is believed to be an autoimmune disease.

In some embodiments, the inflammatory skin disease is an overexposure of the skin to ultraviolet (UV) radiation (sun burn).

Sunburn is a form of radiation burn that affects living tissue, such as skin, that results from an overexposure to ultraviolet (UV) radiation, commonly from the sun. Common symptoms in humans and other animals include red or reddish skin that is hot to the touch, pain, general fatigue, and mild dizziness. Excessive UV radiation is the leading cause of primarily non-malignant skin tumors. Moderate sun tanning without burning can also prevent subsequent sunburn, as it increases the amount of melanin, a photoprotective pigment that is the skin's natural defense against overexposure. In some embodiments, the treatment is a preventative treatment against overexposure of the skin to ultraviolet (UV) radiation (sun burn).

In some embodiments, the treatment is a preventative treatment against melanoma.

Human skin is repeatedly exposed to ultraviolet radiation (UVR) that influences the function and survival of many cell types and is regarded as the main causative factor in the induction of skin cancer. It has been traditionally believed that skin pigmentation is the most important photoprotective factor, since melanin, besides functioning as a broadband UV absorbent, has antioxidant and radical scavenging properties. Besides, many epidemiological studies have shown a lower incidence for skin cancer in individuals with darker skin compared to those with fair skin.

In some embodiments, the ACE2 inhibitor is administered topically.

The invention further relates to a pharmaceutical composition comprising an ACE2 inhibitor for use as a medicament as described herein and one or more pharmaceutically acceptable carriers.

In preferred embodiments, the composition preferably comprises one or more additional pigmentation enhancing agents, such as α-MSH or synthetic α-MSH analogues.

DETAILED DESCRIPTION OF THE INVENTION

Further preferred and non-limiting embodiments of the invention are provided in the detailed description of the invention below. All documents cited herein and any US counterparts are incorporated by reference in their entirety.

The inventors have found, to their knowledge for the first time, that the skin of knockout mice for angiotensin-converting enzyme 2 (ACE2) overexpresses several melanogenic genes and that, accordingly, ACE2-knockout mice on an albino background were not completely white as their controls, but showed a cream coat colour.

ACE2 is a carboxypeptidase that digests peptide substrates with proline at the penultimate position, such as α-melanocyte stimulating hormone (α-MSH). The inventors have found that degradation of α-MSH by ACE2 is normally limiting the effect of the activity of the peptide in the skin. α-MSH is the most potent mediator of melanogenesis and thereby of skin and hair pigmentation. Moreover, its receptor MC1 is a target in several inflammatory skin diseases and for the prevention of melanoma. Thus, ACE2 inhibition in the skin represents a novel strategy for inflammatory skin diseases and for cosmetic applications inducing tanning, by stabilization of α-MSH.

The invention therefore relates to cosmetic and therapeutic methods for modulating pigmentation in a subject, comprising administering a modulator of angiotensin-converting enzyme 2 (ACE2 modulator) to said subject. The invention therefore encompasses methods for both ACE2 inhibitors and ACE2 activators, wherein the ACE2 inhibitor is administered to increase pigmentation in said subject, and the ACE2 activator is administered to decrease pigmentation in said subject.

ACE2 Inhibitors:

Multiple ACE2 inhibitors are known in the art and are accepted as a class of molecule based on its ACE2 inhibitory function. ACE2 activity can be assessed by established methods, such as those described in the prior art. For example, US 20040082496 A1, U.S. Pat. No. 6,632,830 B1, and Huang et al., 2003, all disclose ACE2 inhibitors and functional in vitro and in vivo methods for establishing whether compounds exhibit ACE2-inhibitors activity.

Furthermore, Hernandez Prada et al (Hypertension 2008; 51:1312-1317), WO 2008/066770, Kulemina and Ostrov (Journal of Biomolecular Screening 2011; 16:878-885), Shenoy et al (Am J Respir Crit Care Med Vol 187, Iss. 6, pp 648-657, Mar. 15, 2013), EP 2332582 and WO 2018/140456 disclose ACE2 activators, and screens for identifying ACE2 modulation by small molecules, and therefore also teach functional methods for determining whether any given molecule exerts an ACE2 inhibitory or activating effect.

Also included under the term ACE2 inhibitors are molecules that lead to a down-regulation in ACE2 expression, for example by down-regulation of transcription of the ACE2-encoding gene, or by other means of down-regulating ACE2 expression. ACE2 expression in any given system can be interrogated by appropriate molecular biological techniques, such as qPCR or RT-PCR of ACE2 transcripts, in order to determine whether the administration of any given molecule leads to a reduction in ACE2 expression.

A skilled person is therefore capable of determining whether any given agent falls under the class of ACE2 inhibitors using established functional assays.

All documents and compounds cited therein as ACE2 modulatory, inhibitory or activating compounds, and any US counterparts thereof, are incorporated by reference in their entirety Exemplary, non-limiting embodiments of ACE2 inhibitors include:

According to the present invention, the ACE-2 modulating compound, preferably inhibitor, is in some embodiments an antibody. Antibodies may target and inhibit ACE2. Suitable antibodies may be generated using standard methods by one skilled in art. Alternatively, ACE2 antibodies are commercially available, for example from Abcam (ab108252, ab87436, ab15348, ab108209), or from Sigma Aldrich (HPA000288, SAB2100025, SAB3500346, SAB3500977).

Alternatively, silencing methods may in some embodiments be used to inhibit ACE2, for example using small interfering RNA molecules (siRNA). A skilled person is capable of designing RNA sequences capable of interrupting mRNA encoding ACE2 and leading to its reduced expression, thereby functioning as an ACE2 inhibitor. Validated ACE2 inhibitory RNAs are commercially available, for example from Thermo Fisher Scientific (AM16708, AM16708, AM16708, AM16708, amongst others).

US 20040082496 A1 describes ACE2 modulating compounds suitable for use in the present method, wherein said modulating compounds are preferably ACE2 inhibitors.

In some embodiments, the ACE-2 modulating compound is of the formula (I):

Z-∧      (I)

wherein

Z is a zinc coordinating moiety; and

∧ is an amino-acid mimicking moiety.

In some embodiments, the ACE-2 modulating compound interacts with ACE-2 with a $K_i$ of 1 μM or less. In some embodiments, the said ACE-2 modulating compound interacts with ACE-2 with a $K_i$ of 0.1 μM or less. In some embodiments, the ACE-2 modulating compound interacts with ACE-2 with a $K_i$ of 0.025 μM or less.

In some embodiments, the ACE-2 modulating compound is a compound of the formula:

Z-A-B-E

Wherein Z is a zinc coordinating moiety; E is an enzyme coordinating moiety; A is an auxiliary pocket binding moiety; and B is a side chain binding pocket moiety.

In some embodiments, the ACE-2 modulating compound is a compound of the formula (II):

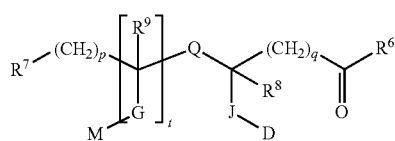

(II)

wherein $R^6$ is hydroxyl or a protecting prodrug moiety;

$R^7$ is a hydrogen atom, carboxylic acid, arylaminocarbonyl, aroyl, aryl, alkylaminocarbonyl, aminocarbonyl, alkenylaminocarboxy, hydroxyl, alkoxy, ether, thiol, amino group heterocycle, or a protecting prodrug moiety;

$R^8$ is hydrogen, or alkyl, and optionally linked to D to form a cyclic structure;

$R^9$ is lower alkyl or hydrogen;

Q is a bond, O, S, $CR^3OH$, $CR^3SH$, $CR^3NR^{3a}R^{3b}$, $NR^3$, $(CR^3R^{3a})_n$, $O(CR^3R^{3b})_n$, and $(CR^3R^{3a})_nO(CR^{3b}R^{3c})_n$, wherein n is 0, 1, 2, or 3 and $R^3$, $R^{3a}$, $R^{3b}$, and $R^{3c}$ are each independently hydrogen, substituted or unsubstituted, branched, cyclic, or straight chain $C_1$-$C_6$ alkyl, $C_2$-$C_6$ alkenyl, acyl, arylalkyl, aryloxycarbonyl, arylaminocarbonyl, arylalkylsulfonyl, or aryl;

G is a linking moiety, or a covalent bond or a $CH_2$, ether, thioether, amine or carbonyl linking moiety;

M is an anchor moiety; or is heteroaryl, substituted with at least one subanchor moiety comprising a substituted or unsubstituted cycloalkyl or aryl ring, linked thereto through a sublinking moiety $(CH_2)_n$ or $(CH_2)_nO(CH_2)_n$ where n is an integer from 0 to 3; wherein the substitution may relate preferably to halogen, preferably Cl, substitution;

J is a bond, an alkyl, alkenyl, or alkynyl moiety;

D is hydrogen, alkoxy, amine, alkyl, alkenyl, alkynyl, aryl, or heteroaryl, optionally linked to G, M or Q to form a ring;

t is 0 or 1;

p is 0, 1, 2, 3, 4, or 5; and q is 0, 1, 2, or 3, and enantiomers, diastereomers, mixtures of enantiomers, mixtures of diastereomers, and pharmaceutically acceptable salts thereof.

In some embodiments, the ACE-2 modulating compound is of the formula (III):

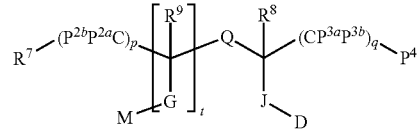

(III)

wherein $P^4$ is selected from the group consisting of a carboxylic acid, cleavable prodrug moieties, $COOP^{4'}$, $(CH_2)_{1-4}SP^{4'}$, or $C(O)NP^4P^{4''}$;

$R^7$ is hydrogen, carboxylic acid, unsubstituted or substituted lower alkyl esters, lower alkenyl esters, dilower alkyl amino esters, arylaminocarbonyl, aroyl, aryl, alkylaminocarbonyl, aminocarbonyl, $COOR^{7'}$, $CONR^{7'}R^{7''}$, hydroxy, ether, thio, amino, $(CH_2)_{1-4}SR^{7'}$, a heterocycle, or a cleavable prodrug moiety;

$P^{4'}$, $P^{4''}$, $R^{7'}$ and $R^{7'}$ are each independently hydrogen, $C_1$-$C_6$alkyl, $C_2$-$C_6$alkenyl, $C_2$-$C_6$alkynyl or optionally substituted aryl;

$R^8$ is selected from the group consisting of hydrogen, alkyl and a covalent bond to D;

$R^9$ is lower alkyl or hydrogen;

Q is a bond, O, S, $CR^3OH$, $CR^3SH$, $CR^3NR^{3a}R^{3b}$, $NR^3$, $(CR^3R^{3a})_n$, $O(CR^3R^{3b})_n$, and $(CR^3R^{3a})_nO(CR^{3b}R^{3c})_n$, wherein n is either 0, 1, 2, or 3, and $R^3$, $R^{3a}$, $R^{3b}$, and $R^{3c}$ are each independently hydrogen, substituted or unsubstituted $C_1$-$C_6$ branched or straight chain alkyl, $C_2$-$C_6$ branched or straight chain alkenyl, aryloxycarbonyl, arylaminocarbonyl, arylalkylsulfonyl, arylalkyl, substituted or unsubstituted acyl, aryl, $C_3$-$C_8$ ring, optionally substituted with up to four heteroatoms;

$P^{2a}$, $P^{2b}$, $P^{3a}$ and $P^{3b}$ are each independently hydrogen, substituted or unsubstituted, branched, straight chain or cyclic $C_1$-$C_5$ alkyl, G is a linking moiety, or a covalent bond or a $CH_2$, ether, thioether, amine or carbonyl linking moiety;

M is an anchor moiety; or is heteroaryl, substituted with at least one subanchor moiety comprising a substituted or unsubstituted cycloalkyl or aryl ring, linked thereto through a sublinking moiety $(CH_2)_n$ or $(CH_2)_nO(CH_2)_n$ where n is an integer from 0 to 3; wherein the substitution may relate preferably to halogen, preferably Cl, substitution;

J is a bond, alkyl, alkenyl, or alkynyl moiety;

D is hydrogen, alkyl, alkenyl, alkynyl, aryl, or optionally linked to G, M, or Q to form a ring;

t is 0 or 1;

p is 0, 1, 2, 3, 4, or 5;

q is 1, 2, or 3; and enantiomers, diastereomers, mixtures of enantiomers, mixtures of diastereomers, and pharmaceutically acceptable salts thereof.

In some embodiments, the ACE-2 modulating compound is of the formula (IV):

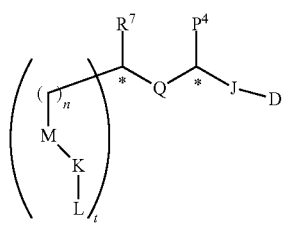

(IV)

wherein

M is carbocyclic, heterocyclic, or CONR'R" wherein R' and R" are each independently hydrogen, $C_1$-$C_6$ alkyl, $C_2$-$C_6$alkenyl, $C_2$-$C_6$alkynyl or optionally substituted aryl;

Q is a bond, O, S, $CR^3OH$, $CR^3SH$, $CR^3NR^{3a}R^{3b}$, $NR^3$, $(CR^3R^{3a})_n$, $O(CR^3R^{3b})_n$, and $(CR^3R^{3a})_nO(CR_{3b}R^{3c})_n$, wherein n is 0, 1, 2, or 3 and $R^3$, $R^{3a}$, $R^{3b}$, and $R^{3c}$ are each independently hydrogen, substituted or unsubstituted, branched, cyclic, or straight chain $C_1$-$C_6$ alkyl, $C_2$-$C_6$ alkenyl, acyl, arylalkyl, aryloxycarbonyl, arylaminocarbonyl, arylalkylsulfonyl, or aryl;

K is an independently selected sublinking moiety for each occurrence;

L is an independently selected subanchor moiety for each occurrence;

$P^4$ is a hydrogen, carboxylic acid, $(CH_2)_{1-4}SP^{4'}$, a cleavable prodrug moiety, carboxylic acid, $COOP^{4'}$, or $CONP^{4'}P^{4''}$;

$R^7$ is hydrogen, carboxylic acid, aroyl, aryl, $COOR^{7'}$, $C(O)NR^{7'}R^{7''}$, hydroxy, ether, thio, $(CH_2)_{1-4}SR^{7'}$, a heterocycle, or a cleavable prodrug moiety;

$P^{4'}$, $P^{4''}$, $R^{7'}$ and $R^{7''}$ independently hydrogen, $C_1$-$C_6$ alkyl, $C_2$-$C_6$alkenyl, $C_2$-$C_6$alkynyl or optionally substituted aryl;

n is 0, 1, 2, 3, or 4;

D is hydrogen, alkyl, alkoxy, alkenyl, amine, hydroxy, alkynyl, aryl, or heteroaryl;

t is 0 or 1, and enantiomers, diastereomers, mixtures of enantiomers, mixtures of diastereomers, and pharmaceutically acceptable salts thereof.

In some embodiments, the ACE-2 modulating compound is of the formula (V):

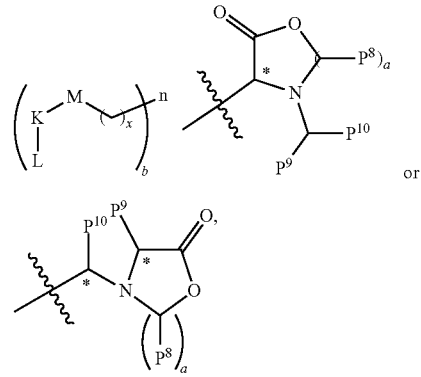

wherein

M is carbocyclic, heterocyclic, or CONR'R" wherein R' and R" are each independently hydrogen, $C_1$-$C_6$ alkyl, $C_2$-$C_6$alkenyl, $C_2$-$C_6$alkynyl or optionally substituted aryl;

K is an independently selected sublinking moiety for each occurrence;

L is an independently selected subanchor moiety for each occurrence;

$P^8$ is hydrogen or alkyl;

$P^9$ is carboxylic acid, unsubstituted or substituted lower alkyl esters, $(CH_2)_{1-4}SP^{9'}$, lower alkenyl esters, dilower alkyl amino esters, lower alkyl amides, dilower alkyl amides, lower alkenyl amides, dilower alkenyl amides, lower alkynyl amides, and aryl amides;

$P^{10}$ is carboxylic acid, unsubstituted or substituted lower alkyl esters, $(CH_2)_{1-4}SP^{10'}$, lower alkenyl esters, dilower alkyl amino esters, lower alkyl amides, dilower alkyl amides, lower alkyl amides, lower alkenyl amides, dilower alkenyl amides, lower alkynyl amides, and aryl amides;

$P^{9'}$ and $P^{10'}$ are each independently alkyl, alkenyl, alkynyl, aryl, or hydrogen;

a is 1, 2, or 3;

b is 0 or 1; and x is 0, 1, 2, 3, or 4, and pharmaceutically acceptable salts thereof.

In some embodiments, the ACE-2 modulating compound is of the formula:

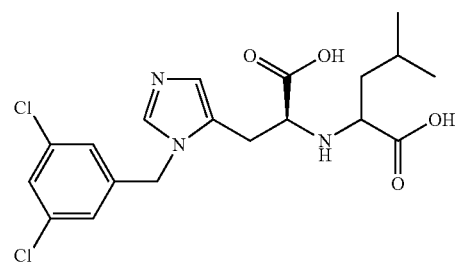 [SMILES: CC(C)CC(N[C@@H](Cc1cncn1Cc1cc(Cl)cc(Cl)c1)C(=O)O)C(=O)O]

In some embodiments, the ACE-2 modulating compound is of the formula:

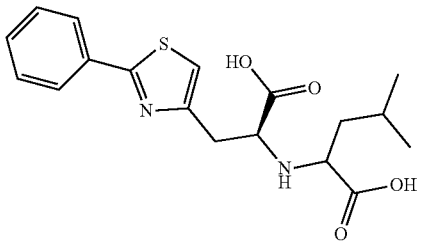 [SMILES: CC(C)CC(N[C@@H](Cc1csc(-c2ccccc2)n1)C(=O)O)C(=O)O]

In some embodiments, the ACE-2 modulating compound is:

2-{1-Carboxy-2-[3-(3-nitro-benzyl)-3H-imidazol-4-yl]ethylamino}-4-methyl-pentanoic acid; 2-[2-(3-Benzyl-3H-imidazol-4-yl)-1-carboxy-ethylamino]-hexanoic acid; 2-[2-(3-Benzyl-3H-imidazol-4-yl)-1-carboxy-ethylamino]-4-methyl-pentanoic acid; 2-[1-Carboxy-2-(1H-imidazol-4-yl)-ethylamino]-4-phenyl-butyric acid; 2-[2-(3-Benzyloxymethyl-3H-imidazol-4-yl)-1-carboxy-ethylamino]-4-methyl-pentanoic acid; 2-[1-Carboxy-2-(methyl-phenyl-amino)-ethylamino]-4-methyl-pentanoic acid; 2-[1-Carboxy-2-(1H-imidazol-4-yl)-ethylamino]-4-methyl-pentanoic acid; 2-[2-(1-Benzyl-1H-imidazol-4-yl)-1-carboxy-ethylamino]-4-methyl-pentanoic acid; 2-(1-Carboxy-2-phenyl-ethylamino)-3-(3H-imidazol-4-yl)-propionic acid; 2-[1-Carboxy-2-(1H-imidazol-4-yl)-ethylamino]-4-methyl-pentanoic acid; 2-[1-Carboxy-2-(4-hydroxy-phenyl)-ethylamino]-3-(1H-imidazol-4-yl)-propionic acid; 2-[1-Carboxy-2-(1H-imidazol-4-yl)-ethylamino]-4-phenyl-butyric acid; 2-[1-Carboxy-2-(1H-imidazol-4-yl)-ethylamino]-pentanoic acid; 2-[2-(1H-Imidazol-4-yl)-1-methoxycarbonyl-ethylamino]-4-methyl-pentanoic acid; 2-(1-Carboxy-3-phenyl-propylamino)-5-pyridin-2-yl-pent-4-ynoic acid; 2-{1-Carboxy-2-[1-(4-chloro-benzyl)-1H-imidazol-4-yl]ethylamino}-4-methyl-pentanoic acid; 2-[2-(1-Benzyl-1H-imidazol-4-yl)-1-carboxy-ethylamino]-4-methyl-pentanoic acid; 2-[1-Carboxy-2-(1H-imidazol-4-yl)-ethylamino]-pentanoic acid; 2-[1-Carboxy-2-(1H-imidazol-4-yl)-ethylamino]-hexanoic acid; 2-(1-Carboxy-2-thiophen-2-yl-ethylamino)-4-methyl-pentanoic acid; 6-Amino-2-(1-carboxy-3-phenyl-propylamino)-hexanoic acid; 2-[1-Carboxy-2-(1H-imidazol-4-yl)-ethylamino]-3-methyl-pentanoic acid; 2-[(Carboxy-phenyl-methyl)-amino]-4-methyl-pentanoic acid; 2-{1-Carboxy-2-[1-(2,4-dinitro-phenyl)-1H-imidazol-4-yl]ethylamino}-4-methyl-pentanoic acid; 2-(1-Carboxy-2-thiazol-2-yl-ethylamino)-4-methyl-pentanoic acid; 2-(1-Carboxy-2-pyridin-2-yl-ethylamino)-4-methyl-pentanoic acid; 2-(1-Carboxy-ethylamino)-3-(1H-imidazol-4-yl)-propionic acid; 2-(1-Carboxy-3-methylsulfanyl-propylamino)-4-phenyl-butyric acid; 2-(1-Carboxy-3-methyl-butylamino)-succinic acid; 2-(1-Carboxy-3-methyl-butylamino)-hexanoic acid; 2-(1-Carboxy-3-methylsulfanyl-propylamino)-4-methyl-pentanoic acid; 2-[1-Carboxy-2-(3-methyl-3H-imidazol-4-yl)-ethylamino]-4-methyl-pentanoic acid; 2-(1-Carboxy-3-phenyl-propylamino)-4-methyl-pentanoic acid; 2-(1-Carboxy-2-phenyl-ethylamino)-4-methyl-pentanoic acid; 2-(1-Carboxy-2-phenyl-ethylamino)-pentanoic acid; 2-(1-Carboxy-2-phenyl-ethylamino)-4-methyl-butyric acid; 2-(1-Carboxy-3-phenyl-propylamino)-4,4-dimethyl-pentanoic acid; 2-(1-Carboxy-ethylamino)-3-(1H-imidazol-4-yl)-propionic acid; 2-(1-Carboxy-2-thiophen-2-yl-ethylamino)-pentanoic acid; 2-[1-Carboxy-2-(1H-[1,2,4]triazol-3-yl)-ethyl amino]-4-methyl-pentanoic acid; 2-(1-Carboxy-2-cyclopropyl-ethylamino)-4-phenyl-butyric acid; 2-[1-Carboxy-2-(4-hydroxy-phenyl)-ethylamino]-3-(1H-imidazol-4-yl)-propionic acid; 2- [2-(1-Benzyl-1H-imidazol-4-yl)-1-carboxy-ethylamino]-4-methyl-pentanoic acid; 2-(1-Carboxy-2-cyclohexyl-ethylamino)-4-phenyl-butyric acid; 2-(1-Carboxy-3-phenyl-propylamino)-5-phenyl-pent-4-ynoic acid; 2-[2-(1H-Imidazol-4-yl)-1-methoxycarbonyl-ethylamino]-4-methyl-pentanoic acid; 2-{1-Carboxy-2-[1-(4-methoxy-benzyl)-1H-imidazol-4-yl]-ethylamino}-4-methyl-pentanoic acid; 2-{1-Carboxy-2-[1-(4-trifluoromethyl-benzyl)-1 H-imidazol-4-yl]-ethylamino}-4-methyl-pentanoic acid; 2-[(Carboxy-phenyl-methyl)-amino]-4-methyl-pentanoic acid; 2-(1-Carboxy-propylamino)-4-methylsulfanyl-butyric acid; and 2-(1-Carboxy-2-phenyl-ethylamino)-4-methyl-pentanoic acid; 2-[2-(1H-Imidazol-4-yl)-1-methoxycarbonyl-ethylamino]-4-methyl-pentanoic acid; 2-{1-Carboxy-2-[1-(4-methoxy-benzyl)-1H-imidazol-4-yl]ethylamino}-4-methyl-pentanoic acid; 2-{1-Carboxy-2-[1-(4-trifluoromethyl-benzyl)-1H-imidazol-4-yl]ethylamino}-4-methyl-pentanoic acid; 2-[(Carboxy-phenyl-methyl)-amino]-4-methyl-pentanoic acid; 2-(1-Carboxy-propylamino)-4-methylsulfanyl-butyric acid; 2-(1-Carboxy-3-phenyl-propylamino)-5-pyridin-2-yl-pent-4-ynoic acid; 2-{1-Carboxy-2-[3-(4-trifluoromethyl-benzyl)-3H-imidazol-4-yl]ethylamino}-4-methyl-pentanoic acid; 2-[1-Carboxy-2-(3-naphthalen-1-ylmethyl-3H-imidazol-4-yl)-ethylamino]-4-methyl-pentanoic acid; 2-{1-Carboxy-2-[3-(4-chloro-benzyl)-3H-imidazol-4-yl]ethylamino}-4-methyl-pentanoic acid; 4-{5-[2-Carboxy-2-(1-carboxy-3-methyl-butylamino)-ethyl]imidazol-1-ylmethyly benzoic acid; 4-{5-[2-Carboxy-2-(1-carboxy-3-methyl-butylamino)-ethyl]-imidazo}-1-ylmethylybenzoic acid; 2-[1-Carboxy-2-(2-phenyl-thiazol-4-yl)-ethylamino]-4-methyl-pentanoic acid; 2-[2-(1-Benzyl-1H-benzoimidazol-2-yl)-1-carboxy-ethylamino]-4-methyl-pentanoic acid; 2-[2-(Benzyl-phenyl-amino)-1-carboxy-ethylamino]-4-methyl-pentanoic acid; 2-[2-(2-Amino-thiazol-4-yl)-1-carboxy-ethylamino]-4-methyl-pentanoic acid; 2-{1-Carboxy-2-[3-(3,4-dichloro-benzyl)-3H-imidazol-4-yl]-ethylamino}-4-methyl-pentanoic acid; 2-[1-Carboxy-2-(2-methyl-thiazol-4-yl)-ethylamino]-4-methyl-pentanoic acid; 2-{1-Carboxy-2-[3-(4-cyano-benzyl)-3H-imidazol-4-yl]ethylamino}-4-methyl-pentanoic acid; 2-{1-Carboxy-2[-3-(3-chloro-benzyl)-3H-imidazol-4-yl]ethylamino}-4-methyl-pentanoic acid; '2-{1-Carboxy-2[-3-(3,5-dichloro-benzyl)-3H-imidazol-4-yl]-ethylamino}-4-methyl-pentanoic acid 2{1-Carboxy-2-[3-(4-methyl-benzyl)-3H-imidazol-4-yl]-ethylamino}-4-methyl-pentanoic acid; 2-{2-[3-(4-Butyl-benzyl)-3H-imidazol-4-yl]-1-carboxy-ethylamino}-4-methyl-pentanoic acid; 2-{1-Carboxy-2-[3-(3,4-dimethyl-benzyl)-3H-imidazol-4-yl]-ethylamino}-4-methyl-pentanoic acid; 2-[2-(2-Benzylamino-thiazol-4-yl)-1-carboxy-ethylamino]-4-methyl-pentanoic acid; 2-{1-Carboxy-2-[3-(3-methyl-benzyl)-3H-imidazol-4-yl]-ethylamino}-4-methyl-pentanoic acid; 2-{1-Carboxy-2-[3-(3,5-dimethyl-benzyl)-3H-imidazol-4-yl]-ethylamino}-4-methyl-pentanoic acid; 2-{1-Carboxy-2-[3-(4-trifluoromethoxy-benzyl)-3H-imidazol-4-yl]-ethylamino}-4-methyl-pentanoic acid; 2-{1-Carboxy-2-[3-(4-isopropyl-benzyl)-3H-imidazol-4-yl]-ethylamino}-4-methyl-pentanoic acid; 2-{1-Carboxy-2-[3-(2-methyl-benzyl)-3H-imidazol-4-yl]-ethylamino}-4-methyl-pentanoic acid; 2-{2-[3-(4-tert-Butyl-benzyl)-3H-imidazol-4-yl]-1-carboxy-ethylamino}-4-methyl-pentanoic acid; 2-{2-[3-(2-Benzenesulfonylmethyl-benzyl)-3H-imidazol-4-yl]-1- carboxy-ethylamino}-4-methyl-pentanoic acid; 2-{1-Carboxy-2-[3-(4-nitro-benzyl)-3H-imidazol-4-yl]-ethylamino}-4-methyl-pentanoic acid; 2-[2-(3-Biphenyl-2-ylmethyl-3H-imidazol-4-yl)-1-carboxy-ethylamino]-4-methyl-pentanoic acid; '2-{2-[3-(3,5-Bis-trifluoromethyl-benzyl)-3H-imidazol-4-yl]-1-carboxy-ethylamino}-4-methyl-pentanoic acid; 2-{1-Carboxy-2-[3-(4-fluoro-benzyl)-3H-imidazol-4-yl]-ethylamino}-4-methyl-pentanoic acid; 2-{1-Carboxy-2-[3-(4-fluoro-benzyl)-3H-imidazol-4-yl]-ethylamino}-4-methyl-pentanoic acid; 2-[1-Carboxy-2-(2-phenyl-thiazol-4-yl)-ethylamino]-4-methyl-pentanoic acid; 2-[1-Carboxy-2-(5-methyl-isoxazol-3-yl)-ethylamino]-4-methyl-pentanoic acid; 2-[2-(1-Benzyl-1H-pyrazol-3-yl)-1-carboxy-ethylamino]-4-methyl-pentanoic acid; 2-{1-Carboxy-2-[3-(2,3-dimethoxy-benzyl)-3H-imidazol-4-yl]-ethylamino}-4-methyl-pentanoic acid; 2-{1-Carboxy-2-[3-(2-methyl-biphenyl-3-ylmethyl)-3H-imidazol-4-yl]-ethylamino}-4-methyl-pentanoic acid; '2-{1-Carboxy-2-[3-(2-methoxy-naphthalen-1-ylmethyl)-3H-imidazol-4-yl]-ethylamino}-4-methyl-pentanoic acid; 2-{1-Carboxy-2-[3-(2,3-difluoro-benzyl)-3H-imidazol-4-yl]-ethylamino}-4-methyl-pentanoic acid; 2-{1-Carboxy-2-[1-(2,3-difluoro-benzyl)-1H-imidazol-4-yl]-ethylamino}-4-methyl-pentanoic acid; 2-{1-Carboxy-2-[3-(2,3-dichloro-benzyl)-3H-imidazol-4-yl]-ethylamino}-4-methyl-pentanoic acid; '2-{1-Carboxy-2-[3-(3-trifluoromethyl-benzyl)-3H-imidazol-4-yl]-ethylamino}-4-methyl-pentanoic acid; 2-{1-Carboxy-2-[3-(2,5-dichloro-benzyl)-3H-imidazol-4-yl]-ethylamino}-4-methyl-pentanoic acid; 2-[1-Carboxy-2-[3-(2,6-dichloro-benzyl)-3H-imidazol-4-yl]-ethylamino}-4-methyl-pentanoic acid; 4-Methyl-2-[1-methylcarbamoyl-2-(3-phenylamino-3H-imidazol-4-yl)-ethylamino]-pentanoic acid; 2[2-(4-Benzyl-furan-3-yl)-1-carboxy-ethylamino]-4-methyl-pentanoic acid; 2-[1-Carboxy-2-(3-phenyl-3H-imidazol-4-yl)-ethylamino]-4-methyl-pentanoic acid; 2-[1-Carboxy-2-(3-phenethyl-3H-imidazol-4-yl)-ethylamino]-4-methyl-pentanoic acid; 2-{1-Carboxy-2-[3-(pyridin-3-yloxy)-3H-imidazol-4-yl]-ethylamino}-4-methyl-pentanoic acid; 2-{1-Carboxy-2-[3-(4-nitro-phenoxy)-3H-imidazol-4-yl]-ethylamino}-4-methyl-pentanoic acid; 2-[1-Carboxy-2-(3-phenoxy-3H-imidazol-4-yl)-ethylamino]-4-methyl-pentanoic acid; 2-{1-Carboxy-2-[3-(2-nitro-benzyl)-3H-imidazol-4-yl]-ethylamino}-4-methyl-pentanoic acid; 2-{1-Carboxy-2-[3-(3-nitro-benzyl)-3H-imidazol-4-yl]-ethylamino}-4-methyl-pentanoic acid; 2-{1-Carboxy-2-[3-(2-trifluoromethyl-benzyl)-3H-imidazol-4-yl]-ethylamino}-4-methyl-pentanoic acid; 2-{1-Carboxy-2-[3-(3-trifluoromethyl-benzyl)-3H-imidazol-4-yl]ethylamino}-4methyl-pentanoic acid; 2-{1-Carboxy-2-[3-(2-methyl-benzyl)-3H-imidazol-4-yl]-ethylamino}-4-methyl-pentanoic acid; 2-{1-Carboxy-2-[3-(3-methyl-benzyl)-3H-imidazol-4-yl]ethylamino}-4-methyl-pentanoic acid; 2-{1-Carboxy-2-[3-(2-chloro-benzyl)-3H-imidazol-4-yl]-ethylamino}-4-methyl-pentanoic acid; 2-{1-Carboxy-2-[3-(3-chloro-benzyl)-3H-imidazol-4-yl]-ethylamino}-4-methyl-pentanoic acid; 2-{1-Carboxy-2-[3-(2-hydroxy-benzyl)-3H-imidazol-4-yl]ethylamino}-4-methyl-pentanoic acid; 2-{1-Carboxy-2-[3-(3-hydroxy-benzyl)-3H-imidazol-4-yl]-ethylamino}-4-methyl-pentanoic acid; 2-{1-Carboxy-2-[3-(2-fluoro-benzyl)-3H-imidazol-4-yl]-ethylamino}-4-methyl-pentanoic acid; 2[2-(3-Benzyl-3H-imidazol-4-yl)-1-carboxy-ethylamino]-4-methyl-pentanoic acid; 2-[1-Carboxy-2-(3-phenylamino-3H-imidazol-4-yl)-ethylamino]-4-methyl-pentanoic acid; 2-{[2,3-Dioxo-1-(3-phenylamino-3H-imidazol-4-ylmethyl)-butyl]-methyl-amino}-4-methyl-pentanoic acid; 2-{[2,3-Dioxo-1-(4-phenylamino-furan-3-ylmethyl)-butyl]-methyl-amino}-4-methyl-pentanoic acid; 2-[2,3-Dioxo-1-(4-phenylamino-furan-3-ylmethyl)-butylamino]-4-methyl-pentanoic acid; 2-[1-Carboxy-2-(4-phenylamino-furan-3-yl)-ethylamino]-4-methyl-pentanoic acid; 2-[1-Carboxy-2-(2-o-tolyl-2H-isoindol-1-yl)-ethylamino]-4-methyl-pentanoic acid; 2-[2-(2-Benzyl-2H-isoindol-1-yl)-1-carboxy-ethylamino]-4-methyl-pentanoic acid; 2-[1-Carboxy-2-(2-phenyl-2H-isoindol-1-yl)-ethylamino]-4-methyl-pentanoic acid; 2-[1-Carboxy-2-(2-pyridin-2-yl-2H-isoindol-1-yl)-ethylamino]-4-methyl-pentanoic acid; 2-{1-Carboxy-2-[2-(3-nitro-phenyl)-2H-isoindol-1-yl]-ethylamino}-4-methyl-pentanoic acid; 2-{1-Carboxy-2-[2-(4-nitro-phenyl)-2H-isoindol-1-yl]-ethylamino}-4-methyl-pentanoic acid; 2-{1-Carboxy-2-[2-(4-nitro-benzyl)-2H-isoindol-1-yl]-ethylamino}-4-methyl-pentanoic acid; 2-({Carboxy-[3-(4-nitro-phenyl)-naphthalen-1-yl]-methyl}-amino)-4-methyl-pentanoic acid; 2-({Carboxy-[3-(4-nitro-benzyl)-naphthalen-1-yl]-methyl}amino)-4-methyl-pentanoic acid; '2-{1-Carboxy-2-[3-(3-trifluoromethyl-benzyl)-3H-imidazol-4-yl4]-ethyl-amino}-4-methyl-pentanoic acid; 2-{1-Carboxy-2-[3-(2,5-dichloro-benzyl)-3H-imidazol-4-yl]-ethylamino}-4-methyl-pentanoic acid; 2-{1-Carboxy-2-[3-(2,6-dichloro-benzyl)-3H-imidazol-4-yl]-ethylamino}-4-methyl-pentanoic acid; 2-[1-Carboxy-2-(3-cyclohexylmethyl-3H-imidazol-4-yl)-ethylamino]-4-methyl-pentanoic acid; 2-[1-Carboxy-2-(3-phenethyl-3H-imidazol-4-yl)-ethylamino]-4-methyl-pentanoic acid; 2-{1-Carboxy-2-[3-(2-ethyl-butyl)-3H-imidazol-4-yl]-ethylamino}-4-methyl-pentanoic acid; 2-{1-Carboxy-2-[3-(3-iodo-benzyl)-3H-imidazol-4-yl]-ethylamino}-4-methyl-pentanoic acid; 2-{1-Carboxy-2-[3-(3-fluoro-benzyl)-3H-imidazol-4-yl]-ethylamino}-4-methyl-pentanoic acid; 2-{1-Carboxy-2-[3-(3-fluoro-benzyl)-3H-imidazol-4-yl]-ethylamino}-4-methyl-pentanoic acid; 2-[1-Carboxy-2-(2-phenylethynyl-1H-imidazol-4-yl)-ethylamino]-4-methyl-pentanoic acid; 2-[1-Carboxy-2-(1-methyl-2-phenylethynyl-1H-imidazol-4-yl)-ethylamino]-4-methyl-pentanoic acid; 2-[1-Carboxy-2-(2-phenethyl-1H-imidazol-4-yl)-ethylamino]-4-methyl-pentanoic acid; 2-[1-Carboxy-3-(3-phenyl-3H-imidazol-4-yl)-propylamino]-4-methyl-pentanoic acid; 2-[1-Carboxy-2-(3-phenyl-3H-imidazol-4-yl)-ethylamino]-4-methyl-pentanoic acid; 2-[2-(3-Benzyl-2,5-dimethyl-3H-imidazol-4-yl)-1-carboxy-ethylamino]-4-methyl-pentanoic acid; 2-[1-Carboxy-4-(3-phenyl-3H-imidazol-4-yl)-butylamino]-4-methyl-pentanoic acid; 2-[2-(2-Benzyl-thiazol-4-yl)-1-carboxy-ethylamino]-4-methyl-pentanoic acid; 2-[1-Carboxy-2-(2-phenyl-oxazol-4-yl)-ethylamino]-4-methyl-pentanoic acid; 2-{1-Carboxy-2-[2-(3,5-dichloro-phenyl)-oxazol-4-yl]-ethylamino}-4-methyl-pentanoic acid; 2-{1-Carboxy-2-[2-(3,5-dimethyl-phenyl)-oxazol-4-yl]-ethylamino}-4-methyl-pentanoic acid; 2-[2-(2-Benzyl-oxazol-4-yl)-1-carboxy-ethylamino]-4-methyl-pentanoic acid; 2-{1-Carboxy-2-[2-(3,5-dichloro-benzyl)-oxazol-4-yl]-ethylamino}-4-methyl-pentanoic acid; 2-{1-Carboxy-2-[2-(3,5-dimethyl-benzyl)-oxazol-4-yl]-ethyl amino}-4-methyl-pentanoic acid; 2-{1-Carboxy-2-[2-(2-cyclohexyl-ethyl)-oxazol-4-yl]-ethylamino}-4-methyl-pentanoic acid; 2-[1-Carboxy-2-(4-phenyl-oxazol-2-yl)-ethylamino]-4-methyl-pentanoic acid; 2-{1-Carboxy-2-[4-(3,5-dichloro-phenyl)-oxazol-2-yl]-ethylamino}-4-methyl-pentanoic acid; 2-{1-Carboxy-2-[4-(3,5-dimethyl-phenyl)-oxazol-2-yl]ethylamino}-4-methyl-pentanoic acid; 2-[2-(4-Benzyl-oxazol-2-yl)-1-carboxy-ethylamino]-4-methyl-pentanoic acid; 2-{1-Carboxy-2-[4-(3,5-dichloro-benzyl)-oxazol-2-yl]-ethylamino}-4-methyl-pentanoic acid; 2-{1-Carboxy-2-[4-(3,5-dimethyl-benzyl)-oxazol-2-yl]-ethylamino}-4- methyl-pentanoic acid; 2-{1-Carboxy-2-[4-(2-cyclohexyl-ethyl)-oxazol-2-yl]-ethylamino}-4-methyl-pentanoic acid; 2-{2-[5-(1H-Benzoimidazol-2-yl)-isoxazol-3-yl]-1-carboxy-ethylamino}-4-methyl-pentanoic acid; 2-{1-Carboxy-2-[1-(3-phenyl-propyl)-1H-[1,2,3]triazol-4-yl]-ethylamino}-4-methyl-pentanoic acid; 2-[1-Carboxy-2-(4-pyridin-4-yl-oxazol-2-yl)-ethylamino]-4-methyl-pentanoic acid; 2-{1-Carboxy-2-[2-(3,5-dichloro-phenyl)-thiazol-4-yl]-ethylamino}-4-methyl-pentanoic acid; 2-{1-Carboxy-2-[2-(3,5-dimethyl-phenyl)-thiazol-4-yl]-ethylamino}-4-methyl-pentanoic acid; 2-[2-(2-Benzyl-thiazol-4-yl)-1-carboxy-ethylamino]-4-methyl-pentanoic acid; 2-{1-Carboxy-2-[2-(3,5-dimethyl-benzyl)-thiazol-4-yl]-ethylamino}-4-methyl-pentanoic acid; 2-{1-Carboxy-2-[2-(3,5-dichloro-benzyl)-thiazol-4-yl]-ethylamino}-4-methyl-pentanoic acid; 2-[1-Carboxy-2-(4-phenyl-thiazol-2-yl)-ethylamino]-4-methyl-pentanoic acid; 2-{1-Carboxy-2-[2-(2-cyclohexyl-ethyl)-thiazol-4-yl]-ethylamino}-4-methyl-pentanoic acid; 2-{1-Carboxy-2-[4-(3,5-dimethyl-phenyl)-thiazol-2-yl]-ethylamino}-4-methyl-pentanoic acid; 2-{1-Carboxy-2-[4-(3,5-dichloro-phenyl)-thiazol-2-yl]-ethylamino}-4-methyl-pentanoic acid; 2-[1-Carboxy-2-(2-pyridin-4-yl-thiazol-4-yl)-ethylamino]-4-methyl-pentanoic acid; 2-[2-(4-Benzyl-thiazol-2-yl)-1-carboxy-ethylamino]-4-methyl-pentanoic acid; 2-{1-Carboxy-2-[4-(3,5-dichloro-benzyl)-thiazol-2-yl]-ethylamino}-4-methyl-pentanoic acid; 2-{1-Carboxy-2-[4-(3,5-dimethyl-benzyl)-thiazol-2-yl]-ethylamino}-4-methyl-pentanoic acid; 2-{1-Carboxy-2-[4-(2-cyclohexyl-ethyl)-thiazol-2-yl]-ethylamino}-4-methyl-pentanoic acid; 2-[1-Carboxy-2-(4-pyridin-4-yl-thiazol-2-yl)-ethylamino]-4-methyl-pentanoic acid; 2-[(3-Benzo[1,3]dioxol-5-yl-propyl)-(2-mercapto-ethyl)-amino]-4-methyl-pentanoic acid; 2-[Cyclohexanecarbonyl-(2-mercapto-ethyl)-amino]-4-methyl-pentanoic acid; 2-[(Benzo[1,2,5]thiadiazol-5-ylmethanesulfonyl)-(2-mercapto-ethyl)-amino]-4-methyl-pentanoic acid; 2-[But-3-enyloxycarbonyl-(2-mercapto-ethyl)-amino]-4-methyl-pentanoic acid; 2-[N'-(1-Benzyl-pyrrolidin-3-yl)-N-(2-mercapto-ethyl)-guanidino]-4-methyl-pentanoic acid; 2-[1-(2-Mercapto-ethyl)-3-(1-phenyl-ethyl)-ureido]-4-methyl-pentanoic acid; 2-[3-Furan-2-ylmethyl-1-(2-mercapto-ethyl)-thioureido]-4-methyl-pentanoic acid; 2-1-Carboxy-2-{2-(3-trifluoromethyl-phenyl)-thiazol-4-yl]-ethylamino}-4-methyl-pentanoic acid; 2-(1-Carboxy-3-methylamino-propylamino)-4-methyl-pentanoic acid; compound with 3-phenyl-propionaldehyde; 2-{1-Carboxy-3-[2-(4-chloro-phenoxy)-acetylamino]-propylamino}-4-methyl-pentanoic acid; 2-[3-(Biphenyl-4-sulfonylamino)-1-carboxy-propylamino]-4-methyl-pentanoic acid; 2-{3-[(Biphenyl-4-carbonyl)-amino]-1-carboxy-propylamino}-4-methyl-pentanoic acid; 2-{1-Carboxy-3-[(naphthalene-2-carbonyl)-amino]-propylamino}-4-methyl-pentanoic acid; 2-[1-Carboxy-3-(4-methoxy-benzenesulfonylamino)-propylamino-4-methyl-pentanoic acid; 2-[1-Carboxy-3-(naphthalene-2-sulfonylamino)-propylamino]-4-methyl-pentanoic acid; 2-[3-(3,5-Bis-trifluoromethyl-benzoylamino)-1-carboxy-propylamino]-4-methyl-pentanoic acid; 2-[3-(3,5-Bis-trifluoromethyl-benzoylamino)-1-carboxy-propylamino]-4-methyl-pentanoic acid; 2-[2-(5-Benzyl-2-methyl-thiazol-4-yl)-1-carboxy-ethylamino]-4-methyl-pentanoic acid; 2-{1-Carboxy-3-[(naphthalene-2-carbonyl)-amino]-propylamino}-2-[3-(Biphenyl-4-sulfonylamino)-1-carboxy-propylamino]-4-methyl-pentanoic acid; 2-{1-Carboxy-2-[2-(2,4-dichloro-phenyl)-thiazol-4-yl]-ethylamino}-4-methyl-pentanoic acid; 2-{1-Carboxy-2-[2-(2,3-dihydro-benzofuran-5-yl)-thiazol-4-yl]-ethylamino}-4-methyl-pentanoic acid; 2-{1-Carboxy-2-[2-(3-chloro-4-fluoro-phenyl)-thiazol-4-yl]-ethylamino}-4-methyl-pentanoic acid; 2-[1-Carboxy-2-(2-p-tolyl-thiazol-4-yl)-ethylamino]-4-methyl-pentanoic acid; 2-[1-Carboxy-2-(5-phenyl-isoxazol-3-yl)-ethylamino]-4-methyl-pentanoic acid; 2-(2-Mercapto-3-phenyl-propionylamino)-4-methyl-pentanoic acid; 2-[1-Carboxy-3-(4-chloro-biphenyl-4-sulfonylamino)-propylamino]-4-methyl-pentanoic acid; 2-[1-Carboxy-3-(3-methoxy-benzoylamino)-propylamino]-4-methyl-pentanoic acid; 2-[1-Carboxy-3-(3-chloro-benzoylamino)-propylamino]-4-methyl-pentanoic acid; 2-[2-(4-Benzyloxy-phenyl)-1-carboxy-ethylamino]-4-methyl-pentanoic acid; 2-[1-Carboxy-2-(4-cyclohexyl-methoxy-phenyl)-ethylamino]-4-methyl-pentanoic acid 2-{1-Carboxy-2-[4-(3,5-dichloro-benzyloxy)-phenyl]-ethylamino}-4-methyl-pentanoic acid; 2-{1-Carboxy-2-[4-(3,5-dimethyl-benzyloxy)-phenyl]-ethylamino}-4-methyl-pentanoic acid; 2-{1-Carboxy-2-[3-(3,4-dichloro-benzyl)-2-oxo-2,3-dihydro-imidazol-1-yl]-ethylamino)-4-methyl-pentanoic acid; 2-[2-(Benzothiazol-2-ylcarbamoyl)-1-carboxy-ethylamino]-4-methyl-pentanoic acid; 2-(1-Carboxy-3-{4-[(4-chloro-phenyl)-phenyl-methyl]-piperazin-1-yl}-3-oxo-propylamino)-4-methyl-pentanoic acid; 2-{2-[3-(3,5-Dichloro-benzyl)-3H-imidazol-4-yl]-1-methoxycarbonyl-ethylamino}-4-methyl-pentanoic acid; 2-({1-Carboxy-2-[3-(3,5-dichloro-benzyl)-3H-imidazol-4-yl]-ethyl}-formyl-amino)-4-methyl-pentanoic acid; 2-{2-[3-(3,5-Dichloro-benzyl)-3H-imidazol-4-yl]-1-methoxycarbonyl-ethylamino}-4-methyl-pentanoic acid benzyl ester; 2-{1-Benzyloxycarbonyl-2-[3-(3,5-dichloro-benzyl)-3H-imidazol-4-yl]ethylamino}-4-methyl-pentanoic acid; 2-{1-Benzyloxycarbonyl-2-[3-(3,5-dichloro-benzyl)-3H-imidazol-4-yl]ethylamino}-4-methyl-pentanoic acid; 2-{1-Butoxycarbonyl-2-[3-(3,5-dichloro-benzyl)-3H-imidazol-4-yl]ethylamino}-4-methyl-pentanoic acid; 2-{1-Carboxy-2-[3-(3,5-dichloro-benzyl)-2-oxo-2,3-dihydro-imidazol-1-yl]-ethylamino}-4-methyl-pentanoic acid 2-{1-Carboxy-2-[3-(3,5-difluoro-benzyl)-2-oxo-2,3-dihydro-imidazol-1-yl]ethylamino}-4-methyl-pentanoic acid; 2-{1-Carboxy-2-[2-oxo-3-(1-phenyl-ethyl)-2,3-dihydro-imidazol-1-yl]ethylamino}-4-methyl-pentanoic acid; 2-[1-Carboxy-2-(3-chloro-benzoylamino)-ethylamino]-4-methyl-pentanoic acid; 2-[1-Carboxy-2-(3,4-dichloro-benzoylamino)-ethylamino]-4-methyl-pentanoic acid; 2-[2-(3-Hydroxy-phenyl)-1-methoxycarbonyl-ethylamino]-4-methyl-pentanoic acid benzyl ester; 2-[2-(3-Hydroxy-phenyl)-1-methoxycarbonyl-ethylamino]-4-methyl-pentanoic acid benzyl ester; 2-[1-Carboxy-2-(2-phenyl-oxazol-4-yl)-ethylamino]-4-methyl-pentanoic acid; 2-[1-Carboxy-2-[2-(3,5-dichloro-phenyl)-oxazol-4-yl]ethylamino}-4-methyl-pentanoic acid; 2-{1-Carboxy-2-[2-(3,5-dichloro-phenyl)-thiazol-4-yl]ethylamino}-4-methyl-pentanoic acid; 2-{1-Carboxy-2-[1-(3,5-dichloro-benzyl)-1H-pyrazol-3-yl]ethylamino}-4-methyl-pentanoic acid; 2-{1-Cyclopentyloxycarbonyl-2-[3-(3,5-dichloro-benzyl)-3H-imidazol-4-yl]ethylamino}-4-methyl-pentanoic acid; 2-{1-Carboxy-2-[3-(3,5-difluoro-benzyl)-2-oxo-imidazolidin-1-yl]ethylamino}-4-methyl-pentanoic acid; 2-[2-(3-Benzyl-2-oxo-2,3-dihydro-imidazol-1-yl)-1-carboxy-ethylamino]-4-methyl-pentanoic acid; 2-[1-Carboxy-2-(4-phenethyloxy-phenyl)-ethylamino]-4-methyl-pentanoic acid; 2-[2-(4-tert-Butoxy-phenyl)-1-carboxy-ethylamino]-4-methyl-pentanoic acid; 2-{1-Carboxy-2-[4-(pyridin-4-ylmethoxy)-phenyl]ethylamino}-4-methyl-pentanoic acid; 2-[2-(4-Allyloxy-phenyl)-1-carboxy-ethylamino]-4-methyl-pentanoic acid; 2-[1-Carboxy-2-{4-(pyridin-3-ylmethoxy)-phenyl]ethyl amino}-4-methyl-pentanoic acid; 2-[1-Carboxy-2-(4'methyl-biphenyl-3-yl)-ethylamino]-4-methyl-pentanoic acid; 2-[1-

Carboxy-2-(3-methoxy-benzoylamino)-ethylamino]-4-methyl-pentanoic acid; 2-{1-Carboxy-2-Rnaphthalene-1-carbonyly amino]-ethylamino}-4-methyl-pentanoic acid; 2-[1-Carboxy-2-(6-chloro-benzothiazol-2-ylcarbamoyl)-ethylamino]-4-methyl-pentanoic acid; 2-[1-Carboxy-2-(5,6-dimethyl-benzothiazol-2-ylcarbamoyl)-ethylamino]-4-methyl-pentanoic acid; 2-[1-Carboxy-2-(4-chloro-benzothiazol-2-ylcarbamoyl)-ethylamino]-4-methyl-pentanoic acid; 2-{1-Carboxy-2-[3-(2-cyclohexyl-ethyl)-2-oxo-2,3-dihydro-imidazol-1-yl]ethylamino}-4-methyl-pentanoic acid; 2-{1-Carboxy-2-[2-oxo-3-(1-phenyl-ethyl)-2,3-dihydro-imidazol-1-yl]ethylamino}-4-methyl-pentanoic acid; 2-[1-Carboxy-2-(5,6-dichloro-benzothiazol-2-ylcarbamoyl)-ethylamino]-4-methyl-pentanoic acid; 2-[1-Carboxy-2-(3-cyclopropylmethyl-2-oxo-2,3-dihydro-imidazol-1-yl)-ethylamino]-4-methyl-pentanoic acid; 2-[1-Carboxy-2-(3',5'-dichloro-biphenyl-3-yl)-ethylamino]-4-methyl-pentanoic acid; 2-[1-Carboxy-2-(3-thiophen-3-yl-phenyl)-thylamino]-4-methyl-pentanoic acid; 2-[1-Carboxy-2-(3',5'-dimethoxy-biphenyl-3-yl)-ethylamino]-4-methyl-pentanoic acid; 3-[2-(1-Benzyloxycarbonyl-3-methyl-butylamino)-2-methoxycarbonyl-ethyl]pyrazole-1-carboxylic acid tert-butyl ester; 2-{2-[3-(3,5-Dichloro-benzyl)-3H-imidazol-4-yl]-1-methoxycarbonyl-ethylamino}-4-methyl-pentanoic acid methyl ester; 2-[1-Carboxy-2-(3-cyclohexyl-2-oxo-2,3-dihydro-imidazol-1-yl) -ethylamino]-4-methyl-pentanoic acid; 2-[1-Carboxy-2-(6-methoxy-benzothiazol-2-ylcarbamoyl)-ethylamino]-4-methyl-pentanoic acid; 2-[1-Carboxy-2-(6-ethoxy-benzothiazol-2-ylcarbamoyl)-ethylamino]-4-methyl-pentanoic acid; 2-[1-Carboxy-2-(6-fluoro-benzothiazol-2-ylcarbamoyl)- ethylamino]-4-methyl-pentanoic acid 2-[2-(6-Bromo-benzothiazol-2-ylcarbamoyl)-1-carboxy-ethylamino]-4-methyl-pentanoic acid 2-{1-Carboxy-2-[3-(3,5-difluoro-phenyl)-2-oxo-2,3-dihydro-imidazol-1-yl]-ethylamino}-4-methyl-pentanoic acid; 2-[1-Carboxy-2-{(naphthalene-2-carbonylyamino]ethylamino}-4-methyl-pentanoic acid; 2-[1-Carboxy-2-(naphthalene-2-sulfonylamino)-ethylamino]-4-methyl-pentanoic acid; 2-{1-Carboxy-2-[2-(3,5-dichloro-benzyl)-2H-pyrazol-3-yl]ethylamino}-4-methyl-pentanoic acid; 2-[1-Carboxy-2-(3-naphthalen-1-yl-phenyl)-ethylamino]-4-methyl-pentanoic acid; 2-[1-Carboxy-2-(3-naphthalen-1-yl-phenyl)-ethylamino]-4-methyl-pentanoic acid; 2-{1-Carboxy-2-[3-(3,5-dichloro-benzyl)-3H-imidazol-4-yl]-ethylamino}-4-methyl-pentanoic acid; 2-{1-Carboxy-2-[3-(3,5-difluoro-benzyloxy)-phenyl]-ethylamino}-4-methyl-pentanoic acid 2-[2-(3-Allyloxy-phenyl)-1-carboxy-ethylamino]-4-methyl-pentanoic acid; 2-{1-Carboxy-2-[3-(3,5-difluoro-phenyl)-2-oxo-imidazolidin-1-yl]ethylamino}-4-methyl-pentanoic acid; 2-{1-Carboxy-2-[(5-chloro-1H-indole-2-carbonyl)-amino]-ethylamino}-4-methyl-pentanoic acid; 2-{1-Carboxy-2-[3-(3,5-dichloro-benzyl)-2-oxo-oxazolidin-4-yl]ethylamino}-4-methyl-pentanoic acid; 2-[1-Carboxy-2-(4-thiophen-3-yl-phenyl)-ethylamino]-4-methyl-pentanoic acid; 2-[1-Carboxy-2-(3',5'-dichloro-biphenyl-4-yl)-ethylamino]-4-methyl-pentanoic acid; 2-[1-Carboxy-2-(4'-methyl-biphenyl-4-yl)-ethylamino]-4-methyl-pentanoic acid 2-{1-Carboxy-2-[3-(4-iodo-benzyl)-3H-imidazol-4-yl]-ethylamino}-4-methyl-pentanoic acid; 2-{1-Carboxy-2-[3-(3,5-difluoro-benzyl)-3H-imidazol-4-yl]ethylamino}-4-methyl-pentanoic acid; 2-(1-Carboxy-2-{3-[2-(4-fluoro-phenyl)-ethyl]-2-oxo-2,3-dihydro-imidazol-1-yl}ethylamino)-4-methyl-pentanoic acid; 2-[1-Carboxy-2-(3-cyclohexylmethyl-2-oxo-2,3-dihydro-imidazol-1-yl)-ethylamino]-4-methyl-pentanoic acid; 2-{1-Carboxy-2-[3-(3,5-dichloro-benzyl)-3H-imidazol-4-yl]ethylamino}-4methyl-pentanoic acid tert-butyl ester; 2-{1-Carboxy-2-[3-(3,5-dichloro-benzyl)-2-oxo-oxazolidin-4-yl]ethylamino}-4-methyl-pentanoic acid; 2-[1-Carboxy-2-(5-p-tolyl-furan-2-yl)-ethylamino]-4-methyl-pentanoic acid; 2-(1-Carboxy-2-{3-[2-(3-fluoro-phenyl)-ethyl]-2-oxo-2,3-dihydro-imidazol-1-yl}ethylamino)-4-methyl-pentanoic acid 2-[1-Carboxy-2-(5-phenyl-furan-2-yl)-ethylamino]-4-methyl-pentanoic acid 2-{1-Carboxy-2-[-5-(3,5-dichloro-phenyl)-furan-2-yl]ethylamino}-4-methyl-pentanoic acid; 2-{1-Carboxy-2-[5-(3,5-dimethyl-phenyl)-furan-2-yl]-ethyl amino}-4-methyl-pentanoic acid 2-{1-Carboxy-2-[5-(3,5-difluoro-phenyl)-furan-2-yl]ethylamino}-4-methyl-pentanoic acid 2-[1-Carboxy-2-(5-thiophen-3-yl-furan-2-yl)-ethylamino]-4-methyl-pentanoic acid 2-[1-Carboxy-2-(6-methyl-benzothiazol-2-ylcarbamoyl)-ethylamino]-4-methyl-pentanoic acid; 2-[1-Carboxy-2-(4-hydroxy-phenyl)-ethylamino]-4-methyl-pentanoic acid; 2-{1-Carboxy-2-[3-(3,5-dichloro-benzyloxy)-phenyl]ethylamino}-4-methyl-pentanoic acid; 2-{1-Carboxy-2-[3-(pyridin-4-ylmethoxy)-phenyl]ethylamino}-4-methyl-pentanoic acid; 2-{1-Carboxy-2-[3-(3,5-dimethyl-benzyloxy)- phenyl]ethylamino}-4-methyl-pentanoic acid; 2-{1-Carboxy-2-[3-(4-chloro-benzyloxy)-phenyl]-ethyl-amino}-4-methyl-pentanoic acid; 2-{2-[3-(2,4-Bis- trifluoromethyl-benzyloxy)-phenyl]-1-carboxy-ethylamino}-4-methyl-pentanoic acid 2-[1-Carboxy-2-(1-phenyl-1H-pyrazol-3-yl)-ethylamino]-4-methyl-pentanoic acid 2-{1-Carboxy-2-[3-(3-chloro-benzyl)-2-oxo-2,3-dihydro-imidazol-1-yl]ethylamino}-4-methyl-pentanoic acid; 2-{1-Carboxy-2-[4-(3,5-dichloro-benzyl)-phenyl]ethylamino}-4-methyl-pentanoic acid; 2-[2-(4-Benzyl-phenyl)-1-carboxy-ethylamino]-4-methyl-pentanoic acid 2-[1-Carboxy-2-(4-phenyl-thiazol-2-ylcarbamoyl)-ethylamino]-4-methyl-pentanoic acid 2-{1-Carboxy-2-[5-(4-methoxy-phenyl)-furan-2-yl]-ethylamino}-4-methyl-pentanoic acid; 2-[2-(5-Benzo[1,3]dioxol-5-yl-furan-2-yl)-1-carboxy-ethylamino]-4-methyl-pentanoic acid 2-[1-Carboxy-2-(5-naphthalen-1-yl-furan-2-yl)-ethylamino]-4-methyl-pentanoic acid; 2-{1-Carboxy-2-[5-(4-chloro-phenyl)-furan-2-yl]ethylamino}-4-methyl-pentanoic acid; 2-{1-Carboxy-2-[5-(4-trifluoromethyl-phenyl)-furan-2-yl]ethylamino}-4-methyl-pentanoic acid; 2-[1-Carboxy-2-(3-isobutoxy-phenyl)-ethylamino]-4-methyl-pentanoic acid; 2-{1-Carboxy-2-[3-(3-ch loro-benzyloxy)-phenyl]-ethylamino}-4-methyl-pentanoic acid; 2-{1-Carboxy-2-[3-(2-chloro-benzyloxy)-phenyl]-ethylamino}-4-methyl-pentanoic acid; 2-[3-(4-Benzyloxy-phenyl)-1-carboxy-propylamino]-4-methyl-pentanoic acid; 2-[3-(4-Benzyloxy-phenyl)-1-carboxy-propylamino]-4-methyl-pentanoic acid; 2-{1-Carboxy-2-[5-(3-chloro-phenyl)-furan-2-yl]ethylamino}-4-methyl-pentanoic a 2-{1-Carboxy-2-[3-(3-fluoro-benzyl)-2-oxo-2,3-dihydro-imidazol-1-yl]ethylamino}-4-methyl-pentanoic acid; 2-{1-Carboxy-2-[3-(3,4-difluoro-benzyl)-2-oxo-2,3-dihydro-imidazol-1-yl]ethylamino}-4-methyl-pentanoic acid; 2-[1-Carboxy-3-(6-fluoro-benzothiazol-2-ylcarbamoyl)-propylamino]-4-methyl-pentanoic acid; 2-{1-Carboxy-2-[3-(2,5-difluoro-benzyl)-2-oxo-2,3-dihydro-imidazol-1-yl]ethylamino}-4-methyl-pentanoic acid; 2-{1-Carboxy-2-[4-(3,5-difluoro-benzoylamino)-phenyl]ethylamino}-4-methyl-pentanoic acid; 2-[1-Carboxy-2-(4'-fluoro-biphenyl-4-yl)-ethylamino]-4-methyl-pentanoic acid; 2-[2-(4-Benzo[1,3]dioxo1-5-yl-phenyl)-1-carboxy-ethylamino]-4-methyl-pentanoic acid; 2-[2-(4-Benzo [b]thiophen-3-yl-phenyl)-1-carboxy-ethylamino]-4-methyl-pentanoic acid; 2-[2-(3-Benzyl-phenyl)-1-carboxy-ethylamino]-4-methyl-pentanoic acid; 2-[1-Carboxy-2-(4'-trifluoromethyl-biphenyl-4-yl)-ethylamino]-4-methyl- pentanoic acid; 2-(1-Carboxy-2-{3-[2-(3-chloro-phenyl)-ethyl]-2-oxo-2,3-dihydro-imidazol-1- yl}ethylamino)-4-methylpentanoic acid; 2-{2-[3-(4-Bromo-benzyl)-3H-imidazol-4-yl]-1-carboxy-ethylamino}-4-pentanoic acid; 2-[2-(4-Benzenesulfonylamino-phenyl)-1-carboxy-ethylamino]- 4-methyl-pentanoic acid 2-{1-Carboxy-2-[3-(3-chloro-benzyl)-phenyl]ethylamino}-4-methyl-pentanoic acid 2-{1-Carboxy-2-[3-(3,5-dichloro-benzyl)-phenyl]ethylamino}-4-methyl-pentanoic acid 2-{1-Carboxy-2-[3-(5-chloro-benzo[b]thiophen-3-ylmethoxy)-phenyl]-ethylamino}-4-methyl-pentanoic acid; 2-[1-Carboxy-2-(4-pyridin-2-yl-phenyl)-ethylamino]-4-methyl-pentanoic acid; 2-[1-Carboxy-2-(4-pyridin-3-yl-phenyl)-ethylamino]-4-methyl-pentanoic acid; 2-[1-Carboxy-2-(4-pyridin-4-yl-phenylethylamino]-4-methyl-pentanoic acid; 2-(1-Carboxy-ethylamino)-3-[3-(3,5-dichloro-benzyl)-3H-imidazol-4-yl]propionic acid; 2-(1-Carboxy-ethylamino)-3-[3-(3,5-dichloro-benzyl)-3H-imidazol-4-yl]propionic acid; 2-{1-Carboxy-2-[3-(3,5-dichloro-benzyl)-3H-imidazol-4-yl]-ethylamino}-4-phenyl-butyric acid; 2-{1-Carboxy-2-[3-(3,5-dichloro-benzyl)-3H-imidazol-4-yl]ethylamino}-4-phenyl-butyric acid; 2-(1-Carboxy-2-{3-[2-(2-fluoro-phenyl)-ethyl]-2-oxo-2,3-dihydro-imidazol-1-ylethylamino)-4-methyl-pentanoic acid; 2-[1-Carboxy-2-(4-pyrrol-1-yl-phenyl)-ethyl amino]-4-methyl-pentanoic acid; 2-(1-Carboxy-3-methyl-butylamino)-5-(3,5-dichloro-phenyl)-pent-4-ynoic acid; 2-{1-Carboxy-2-[4-(3,5-difluoro-phenoxy)-phenyl]-ethylamino}-4-methyl-pentanoic acid; 2-[1-Carboxy-2-(3',5'-dichloro-biphenyl-2-yl)-ethylamino]-4-methyl-pentanoic acid; 4-[2-Carboxy-2-(1-carboxy-3-methyl-butylamino)-ethyl]-benzoic acid tert-butyl ester; 2-(1-Carboxy-3-methyl-butylamino)-5-(3,5-dichloro-phenyl)-pent-4-enoic acid; 2-{1-Carboxy-2-[3-(3,5-difluoro-benzyl)-2,5-dioxo-imidazolidin-1-yl]ethylamino}-4-methyl-pentanoic acid; 2-{1-Carboxy-2-[3-(3,5-dichloro-benzyl)-2,5-dioxo-imidazolidin-1-yl]ethylamino}-4-methyl-pentanoic acid; 2-{2-[3-(2,4-Bis-trifluoromethyl-benzyl)-2,5-dioxo-imidazolidin-1-yl]-1-carboxy-ethylamino}-4-methyl-pentanoic acid; 2-{1-Carboxy-2-[4-(5-methyl-pyridin-2-yl)-phenyl]ethylamino}-4-methyl-pentanoic acid; 2-[1-Carboxy-2-[4-(4-methyl-pyridin-2-yl)-phenyl]ethylamino}-4-methyl-pentanoic acid; 2-{1-Carboxy-2-[4-(3-chloro-4-ethoxy-pyridin-2-yl)-phenyl]ethylamino}-4-methyl-pentanoic acid; 2-[1-Carboxy-2-(4-quinolin-3-yl-phenyl)-ethylamino]-4-methyl-pentanoic acid; 2-{1-Carboxy-2-[4-(3,5-difluoro-benzylcarbamoyl)-phenyl]-ethylamino}-4-methyl-pentanoic acid; 2-{1-Carboxy-2-[4-(3,5-dichloro-phenylcarbamoyl)-phenyl]ethylamino}-4-methyl-pentanoic acid; 241-Carboxy-2-(4-phenylcarbamoyl-phenyl)-ethylamino]-4-methyl-pentanoic acid; 2-[1-Carboxy-2-(4-cyclohexylcarbamoyl-phenyl)-ethylamino]-4-methyl-pentanoic acid; 2-[1-Carboxy-2-(2-cyano-phenyl)-ethylamino]-4-methyl-pentanoic acid; 2-[1-Carboxy-2-(4-phenoxy-phenyl)-ethylamino]-4-methyl-pentanoic acid; 2-{1-Carboxy-2-[4-(5-chloro-benzo[b]thiophen-3-ylmethoxy)-phenyl]-ethylamino}-4-methyl-pentanoic acid;

2-{1-Carboxy-2-[5-(3,4-dichloro-phenyl)-isoxazol-3-yl]ethylamino}-4-methyl-pentanoic acid; 2-{1-Carboxy-2-[4-(3,5-dichloro-phenoxy)- phenyl]-ethylamino}-4-methyl-pentanoic acid; 2-{1-Carboxy-2-[2-(3,5-dichloro-phenoxy)-phenyl]-ethylamino}-4-methyl-pentanoic acid; 2-{1-Carboxy-2-[2-(3-chloro-benzyloxy)-phenyl]ethylamino}-4-methyl-pentanoic acid; 2-{1-Carboxy-2-[4-(4-fluoro-phenoxy)-phenyl]-ethylamino}-4-methyl-pentanoic acid; 2-[1-Carboxy-2-(1-p-tolyl-1H-pyrazol-3-yl)-ethylamino]-4-methyl-pentanoic acid; 2-{1-Carboxy-2-[4-(cyclopentanecarbonyl-amino)-phenyl]ethylamino}-4-methyl-pentanoic acid; 2-{1-Carboxy-2-[4-(2,2-dimethyl-propionylamino)-phenyl]ethylamino}-4-methyl-pentanoic acid; 2-{1-Carboxy-2-[2-(5-chloro-benzo[b]thiophen-3-ylmethoxy)-phenyl]-ethylamino}-4-methyl-pentanoic acid; 2-{1-Carboxy-2-[5-(4-chloro-phenyl)-isoxazol-3-yl]ethylamino}-4-methyl-pentanoic acid; 2-{1-Carboxy-2-[5-(2-chloro-phenyl)-isoxazol-3-yl]-ethylamino}-4-methyl-pentanoic acid; 2-{1-Carboxy-2-[4-(5-fluoro-2,3-dihydro-benzofuran-3-ylmethoxy)-phenyl]-ethylamino}-4-methyl-pentanoic acid; 2-{2-[4-(Benzo[b]thiophen-3-ylmethoxy)-phenyl]-1-carboxy-ethylamino}-4-methyl-pentanoic acid; 5-[2-Carboxy-2-(1-carboxy-3-methyl-butylamino)-ethyl]-1-(3,5-dichloro-benzyl)-1H-pyrrole-2-carboxylic acid; 2-{1-Carboxy-2-[1-(2-cyclohexyl-ethyl)-5-(2,2,2-trifluoro-acetyl)-1H-pyrrol-2-yl]ethylamino}-4-methyl-pentanoic acid; 2-[1-Carboxy-2-(4-nitro-phenyl)-ethylamino]-4-methyl-pentanoic acid; 2-{1-Carboxy-2-[4-(2-methoxy-benzoylamino)-phenyl]-ethylamino}-4-methyl-pentanoic acid; 2-[1-Carboxy-2-(2-trifluoromethyl-phenyl)-ethylamino]-4-methyl-pentanoic acid; 2-(2-{4-[Bis-(3,5-difluoro-benzyl)-amino]-phenyl}-carboxy-ethylamino)-4-methyl-pentanoic acid; 2-[1-Carboxy-2-(2-p-tolyl-thiazol-4-yl)-ethylamino]-4-phenyl-butyric acid; 2-[1-Carboxy-2-(4-dimethylcarbamoyl-phenyl)-ethylamino]-4-methyl-pentanoic acid; 2-{1-Carboxy-2-[4-(3,5-dimethyl-phenylcarbamoyl)-phenyl]ethylamino}-4-methyl-pentanoic acid; 2-[2-(4-tert-Butylcarbamoyl-phenyl)-1-carboxy-ethyl-amino]-4-methyl-pentanoic acid; 4-Methyl-2-{[pyrimidin-2-yl-(2-p-tolyl-thiazol-4-ylmethyl)-amino]-methylypentanoic acid; 2-1-Carboxy-2-[1-(3,5-dichloro-benzyl)-1H-pyrrol-2-yl]-ethylamino}-4-methyl-pentanoic acid; 2-[1-Carboxy-2-(4-isopropylcarbamoyl-phenyl)-ethylamino]-4-methyl-pentanoic acid; 2-{1-Carboxy-2-[4-(morpholine-4-carbonyl)-phenyl]-ethylamino}-4-methyl-pentanoic acid; and 2-1-Carboxy-2-[4-(3,4-dihydro-1H-isoquinoline-2-carbonyl)-phenyl]-ethylamino}-4-methyl-pentanoic acid.

WO 2010093804 A1 describes ACE2 modulating compounds suitable for use in the present method, wherein said modulating compounds are preferably ACE2 inhibitors.

In some embodiments, the ACE2 inhibitor has the formula (VI):

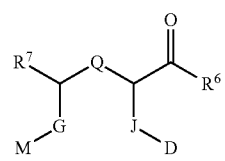

(VI)

wherein $R^6$ is hydroxyl or a protecting prodrug moiety;

$R^7$ is hydrogen, carboxylic acid, ether, alkoxy, an amide, a protecting prodrug moiety, hydroxyl, thiol, heterocyclyl, alkyl or amine;

Q is $CH_2$, O, NH or $NR^3$, wherein $R^3$ is substituted or unsubstituted C1-5 branched or straight chain alkyl, C2-5 branched or straight chain alkenyl, substituted or unsubstituted acyl, aryl or a C3-5 ring;

G is a covalent bond or a $CH_2$, ether, thioether, amine or carbonyl linking moiety;

M is heteroaryl, substituted with at least one subanchor moiety comprising a substituted or unsubstituted cycloalkyl or aryl ring, linked thereto through a sublinking moiety $(CH_2)_n$ or $(CH_2)_nO(CH_2)_n$ where n is an integer from 0 to 3;

J is a bond or a substituted or unsubstituted alkyl, alkenyl or alkynyl moiety; and D is alkyl, alkenyl, alkynyl, aryl or heteroaryl, optionally linked to G or M to form a ring; or a pharmaceutically acceptable salt or prodrug thereof.

In some embodiments, the ACE2 inhibitor is selected from the group consisting of 2-[I-carboxy-2-[3-(4-trifluoromethylbenzyl)-3H-imidazol-4-yl]ethylamino]-4-methyl-pentanoic acid; 2-[1-carboxy-2-[3-naphthalen-1-ylmethyl-3H-imidazol-4-yl]ethylamino]-4-methyl-pentanoic acid; 2-[I-carboxy-2-[3-(4-chlorobenzyl)-3H- imidazol-4-yl]ethylamino]-4-methylpentanoic acid; 2-[I-carboxy-2-[3-(3,4-dichlorobenzyl)-3H-imidazol-4-yl]ethylamino]-4-methyl-pentanoic acid; 2-[I-carboxy-2-[3-(4-cyanobenzyl)-3H-imidazol-4-yl]ethylamino]-4-methylpentanoic acid; -[I-carboxy-2-[3-(3-chlorobenzyl)-3H-imidazol-4-yl]ethylamino]-4-methylpentanoic acid; -[I-carboxy-2-[3-(3,5-dichlorobenzyl)-3H-imidazol-4-yl]ethylamino]-4-methyl-pentanoic acid; -[I-carboxy-2-[3-(4-methylbenzyl)-3H-imidazol-4-yl]ethylamino]-4-methylpentanoic acid; -[I-carboxy-2-[3-(3,4-dimethylbenzyl)-3H-imidazol-4-yl]ethylamino]-4-methyl-pentanoic acid; -[I-carboxy-2-[3-(3-methylbenzyl)-3H-imidazol-4-yl]ethylamino]-4-methylpentanoic acid; -[I-carboxy-2-[3-(3,5-dimethylbenzyl)-3H-imidazol-4-yl]ethylamino]-4-methyl-pentanoic acid; -[I-carboxy-2-[3-(4-trifluoromethoxybenzyl)-3H-imidazol-4-yl]ethylamino]-4-methyl-pentanoic acid; -[I-carboxy-2-[3-(4-isopropylbenzyl)-3H-imidazol-4-yl]ethylamino]-4-methyl-pentanoic acid; -[I-carboxy-2-[3-(4-tert-butylbenzyl)-3H-imidazol-4-yl]ethylamino]-4-methyl-pentanoic acid; -[I-carboxy-2-[3-(4-nitrobenzyl)-3H-imidazol-4-yl]ethylamino]-4-methylpentanoic acid; -[I-carboxy-2-[3-(2,3-dimethoxybenzyl)-3H-imidazol-4-yl]ethylamino]-4-methyl-pentanoic acid; -[I-carboxy-2-[3-(2,3-difluorobenzyl)-3H-imidazol-4-yl]ethylamino]-4-methyl-pentanoic acid; -[I-carboxy-2-[3-(2,3-dichlorobenzyl)-3H-imidazol-4-yl]ethylamino]-4-methyl-pentanoic acid; -[I-carboxy-2-[3-(3-trifluoromethylbenzyl)-3H-imidazol-4-yl]ethylamino]-4-methyl-pentanoic acid; -[2-(3-benzo[I,3]dioxol-5-ylmethyl-3H-imidazol-4-yl)-I-carboxyethylamino]-4-methylpentanoic acid; -[I-carboxy-2-[3-(2-cyclohexylethyl)-3H-imidazol-4-yl]ethylamino]-4-methyl-pentanoic acid; 2[I-carboxy-2-[3-phenethyl-3H-imidazol-4-yl]ethylamino]-4-methylpentanoic acid; 2-[I-carboxy-2-[3-(3-iodobenzyl)-3H-imidazol-4-yl]ethylamino]-4-methylpentanoic acid; 2-[I-carboxy-2-[3-(3-fluorobenzyl)-3H-imidazol-4-yl]ethylamino]-4-methylpentanoic acid; 2-[I-carboxy-2-[3-benzyloxymethyl-3H-imidazol-4-yl]ethylamino]-4-methylpentanoic acid; 2-[I-carboxy-2-[3-(4-butylbenzyl)-3H-imidazol-4-yl]ethylamino]-4-methylpentanoic acid; 2-[I-carboxy-2-[3-(2-methylbenzyl)-3H-imidazol-4-yl]ethylamino]-4-methylpentanoic acid; 2-[I-carboxy-2[2-phenylthiazol-4-yl]ethylamino]-4-methylpentanoic acid; 2-[1-carboxy-2-[1-benzyl)-1H-pyrazol-4-yl]ethylamino]-4-methylpentanoic acid; 2-[I-carboxy-2-[3-(2-methylbiphenyl-3-ylmethyl)-3H-imidazol-4-yl]ethylamino]-4-methylpentanoic acid; and pharmaceutically acceptable salts thereof.

In some embodiments, the ACE2 inhibitor is (S,S)-2-[I-carboxy-2-[3-(3,5-dichlorobenzyl)-3H-imidazol-4-yl]- ethylamino]-4-methylpentanoic acid (OREIOOI), pharmaceutically acceptable salts thereof and prodrugs thereof.

In some embodiments, the ACE2 inhibitor is (2S)-2-[[(1S)-1-carboxy-2-[3-[(3,5-dichlorophenyl)methyl]imidazol-4-yl]ethyl]amino]-4-methylpentanoic acid, also known as GL1001 or MLN 4760.

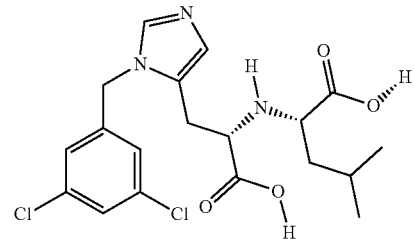

Huang et al (The Journal of Biological Chemistry Vol. 278, No. 18, Issue of May 2, pp. 15532-15540, 2003) disclose Novel Peptide Inhibitors of Angiotensin-converting Enzyme 2.

TABLE II of Huang et al discloses a number of peptidic inhibitors suitable for use in the present invention. Sequences of synthesized peptides (Sequence; Ac-denotes N-terminal acetylation; -NH2 denotes C-terminal amidation):

```
DX500 Ac-GSNRECHALFCMDFAPGEGGG-NH2
(SEQ ID NO 1)

DX501 Ac-GSSPTCRALFCVDFAPGEGGG-NH2
(SEQ ID NO 2)

DX502 Ac-GSLEMCEALFCVEFAPGEGGG-NH2
(SEQ ID NO 3)

DX507 Ac-GSNDYCTVFTGALFCLDFAPEGGG-NH2
(SEQ ID NO 4)

DX514 Ac-GSPNQCGVDIWALFCVDFAPEGGGK-NH2
(SEQ ID NO 5)

DX504 Ac-AGEGNCFLIGPWCFEFGTEGGG-NH2
(SEQ ID NO 6)

DX508 Ac-GSYDNCLGLANLNFCFDFAPEGGG-NH2
(SEQ ID NO 7)

DX510 Ac-GDDDDCGWIGFANFHLCLHGDPEGGG-NH2
(SEQ ID NO 8)

DX511 Ac-GDPFECDWGPWTLEMLCGPPDPEGGG-NH2
(SEQ ID NO 9)

DX524 Ac-GSRIGCRDSRCNWWAPGEGGG-NH2
(SEQ ID NO 10)

DX525 Ac-GSRGFCRDSSCSFPAPGEGGG-NH2
(SEQ ID NO 11)

DX526 Ac-GSWPTCLTMDCVYNAPGEGGG-NH2
(SEQ ID NO 12)

DX527 Ac-AGWVLCFEWEDCDEKGTEGGG-NH2
(SEQ ID NO 13)

DX528 Ac-AGVYFCFDWEQDCDEMGTEGGG-NH2
(SEQ ID NO 14)

DX529 Ac-AGWEVCHWAPMMCKHGGTEGGG-NH2
(SEQ ID NO 15)

DX530 Ac-AGQKECKFGYPHCLPWGTEGGG-NH2
(SEQ ID NO 16)

DX531 Ac-AGSDWCGTWNNPCFHQGTEGGG-NH2
(SEQ ID NO 17)

DX512 Ac-GDRLHCKPQRQSPWMKCQHLDPEGGG-NH2
(SEQ ID NO 18)
```

TABLE II-continued of Huang et al discloses a number of peptidic inhibitors suitable for use in the present invention. Sequences of synthesized peptides (Sequence; Ac-denotes N-terminal acetylation; -NH2 denotes C-terminal amidation):

DX513 Ac-GDLHACRPVRGDPWWACTLGDPEGGG-NH2
(SEQ ID NO 19)

DX599 Ac-GDRYLCLPQRDKPWKFCNWFDPEGGG-NH2
(SEQ ID NO 20)

DX600 Ac-GDYSHCSPLRYYPWWKCTYPDPEGGG-NH2
(SEQ ID NO 21)

DX601 Ac-GDGFTCSPIRMFPWFRCDLGDPEGGG-NH2
(SEQ ID NO 22)

DX602 Ac-GDFSPCKALRHSPWWVCPSGDPEGGG-NH2
(SEQ ID NO 23)

Most preferred are DX512, 513, 599, 600, 601 or 602. The most potent inhibitor, DX600, had a Ki of 2.8 nM. Steady-state enzyme kinetic analysis showed that these potent ACE2 inhibitors exhibited a mixed competitive and non-competitive type of inhibition. They were not hydrolyzed by ACE2. Furthermore, they did not inhibit ACE activity, and thus were specific to ACE2. Finally, they also inhibited ACE2 activity toward its natural substrate angiotensin I, suggesting that they would be functional in vivo.

Mores et al (J. Med. Chem. 2008, 51, 2216-2226) disclose further ACE2 inhibitors potentially suitable for use in the present invention. For example, compounds 40 and 41 disclosed therein show strong ACE2 inhibition.

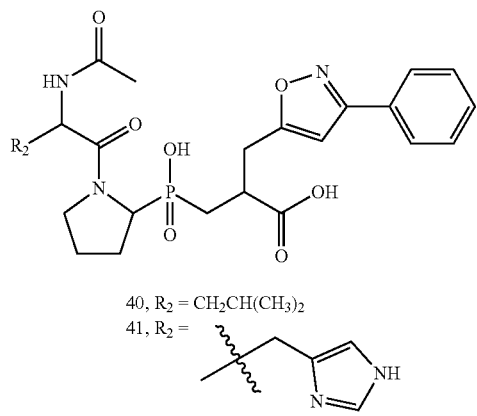

40, R$_2$ = CH$_2$CH(CH$_3$)$_2$
41, R$_2$ =

Further ACE2 inhibitors of of Mores et al potentially show the desired activity. Potent and selective inhibitors of ACE2, which have been identified by evaluating a series of phosphinic di- and tripeptides of the general formula: Z-Xaa(PO2-CH2)YaaOH and Ac-Zaa-Xaa(PO2-CH2)YaaOH. The most potent inhibitor (41) in this series is a tripeptide that displays a Ki value of 0.4 nM toward ACE2.

ACE2 Activators:

Multiple ACE2 activators are known in the art and are accepted as a class of molecule based on its ACE2 activating function. ACE2 activity can be assessed by established methods, such as those described in the prior art. For example, US 20040082496 A1, U.S. Pat. No. 6,632,830 B1, and Huang et al., 2003, all disclose ACE2 inhibitors and functional in vitro and in vivo methods for establishing whether compounds exhibit ACE2 modulatory activity.

Furthermore, Hernandez Prada et al (Hypertension 2008; 51:1312-1317), WO 2008/066770, Kulemina and Ostrov (Journal of Biomolecular Screening 2011; 16:878-885), Shenoy et al (Am J Respir Crit Care Med Vol 187, Iss. 6, pp 648-657, Mar. 15, 2013), EP 2332582 and WO 2018/140456 disclose ACE2 activators, and screens for identifying ACE2 modulation by small molecules, and therefore also teach functional methods for determining whether any given molecule exerts an ACE2 activating effect.

In particular, ACE2 activity can be assessed as described in Kulemina and Ostrov (Journal of Biomolecular Screening 2011; 16:878-885).

Also included under the term ACE2 activators are molecules that lead to an up-regulation in ACE2 expression, for example by up-regulation of transcription of the ACE2-encoding gene, or by other means of up-regulating ACE2 expression. ACE2 expression in any given system can be interrogated by appropriate molecular biological techniques, such as qPCR or RT-PCR of ACE2 transcripts, in order to determine whether the administration of any given molecule leads to an increase in ACE2 expression.

A skilled person is therefore capable of determining whether any given agent falls under the class of ACE2 activators using established functional assays.

Exemplary, non-limiting embodiments of ACE2 activators include:

Hernandez Prada et al (Hypertension 2008; 51:1312-1317) describe Small-Molecule Angiotensin-Converting Enzyme 2 Activators xanthenone and resorcinolnaphthalein that enhance ACE2 activity in a dose-dependent manner and may be suitable for treating cardiovascular disease, hypertension or lung injury. The structures are provided below:

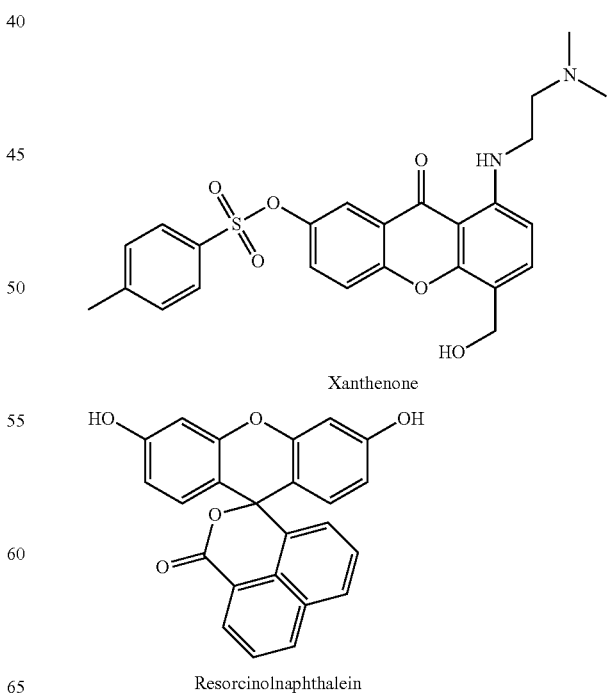

Xanthenone

Resorcinolnaphthalein

In a related aspect, the ACE2 activator is represented by Formula (VII) as in WO 2008/066770:

$$Ar—(Y)_n \qquad (VII)$$

wherein,

Ar is a polycyclic fused aromatic moiety; Y represents a hydrogen bond donor or acceptor; and n is an integer from 2 to 8; or a pharmaceutically acceptable salt or prodrug thereof.

In certain embodiments, Ar is a polycyclic moiety having at least two, three, four, five, or six fused rings, including spirocyclic rings. In certain embodiments, each hydrogen bond donor or acceptor is independently selected from the group consisting of —OH, O-alkyl, O-aryl; $NH_2$, NH-alkyl, NH-aryl; N(alkyl)(aryl), N(alkyl)$_2$; N(aryl)$_2$; COON; COO-alkyl; or a salt thereof.

In certain embodiments of formula VII, Ar may be substituted with one or more groups selected from: alkyl (e.g., lower alkyl), alkenyl, alkynyl, alkylaryl, aryl (including heteroaryl), halogen, hydroxyl, alkoxy, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, and alkylaryl.

In certain embodiments, the compound is represented by Formula (VIII) as in WO 2008/066770:

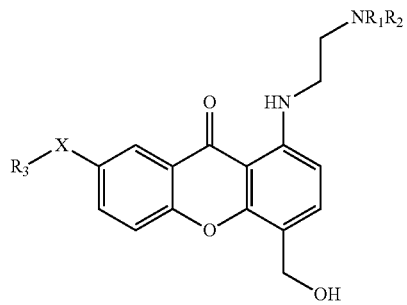

in which X is O or S; R1 and R2 are independently hydrogen, optionally substituted C1-C8alkyl, optionally substituted C3-C8cycloalkyl, optionally substituted C2-C8 alkenyl, optionally substituted C2-C8 alkynyl, optionally substituted C1-C8 alkanoyl, or optionally substituted aryl; and R3 is optionally substituted C1-C8 alkyl, optionally substituted C3-C8 cycloalkyl, optionally substituted C2-C8 alkenyl, optionally substituted C2-C8 alkynyl, optionally substituted C1-C8 alkanoyl, optionally substituted C1-C8 alkanoyl or optionally substituted C1-C8 alkylsulfonyl, optionally substituted C1-C8 arylsulfonyl, or optionally substituted aryl; or a pharmaceutically acceptable salt or prodrug thereof.

In certain embodiments of Formula (VIII), R1 and R2 are each methyl. In certain embodiments of Formula (VIII), X is O. In certain embodiments of Formula (VIII), R3 is optionally substituted C1-C8 alkanoyl. In certain embodiments of Formula (VIII), R3 is optionally substituted C1-C8 arylsulfonyl. In certain embodiments of Formula (VIII), the compound is not 14[2-(diethylamino)ethyl]amino]-4-(hydroxymethyl)-7-[[(4-methylphenyl)sulfonyl]oxy]-9H-xanthen-9-one.

In further embodiments, the compound is selected from those in WO 2008/066770, for example:

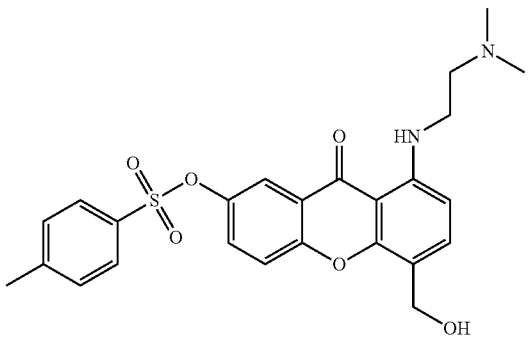

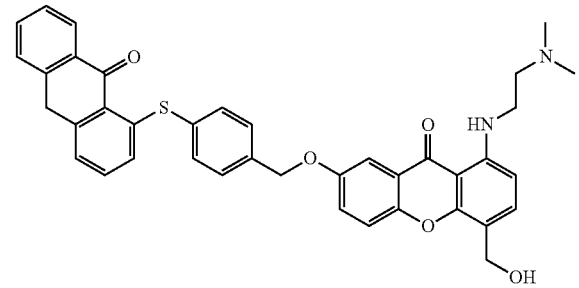

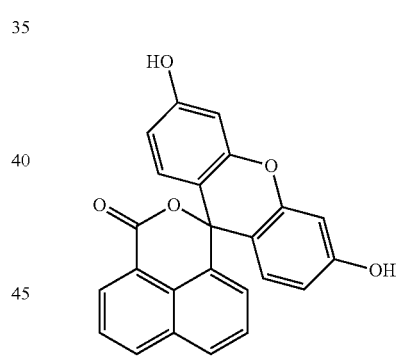

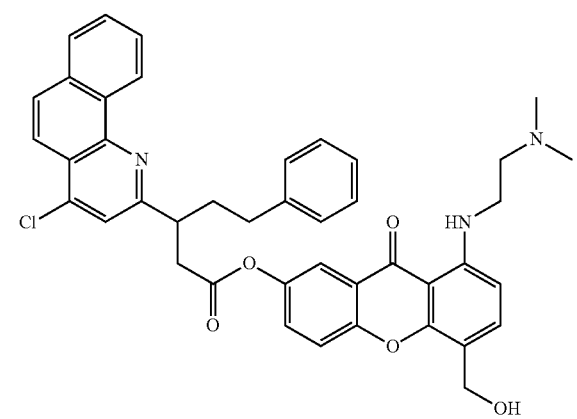

-continued

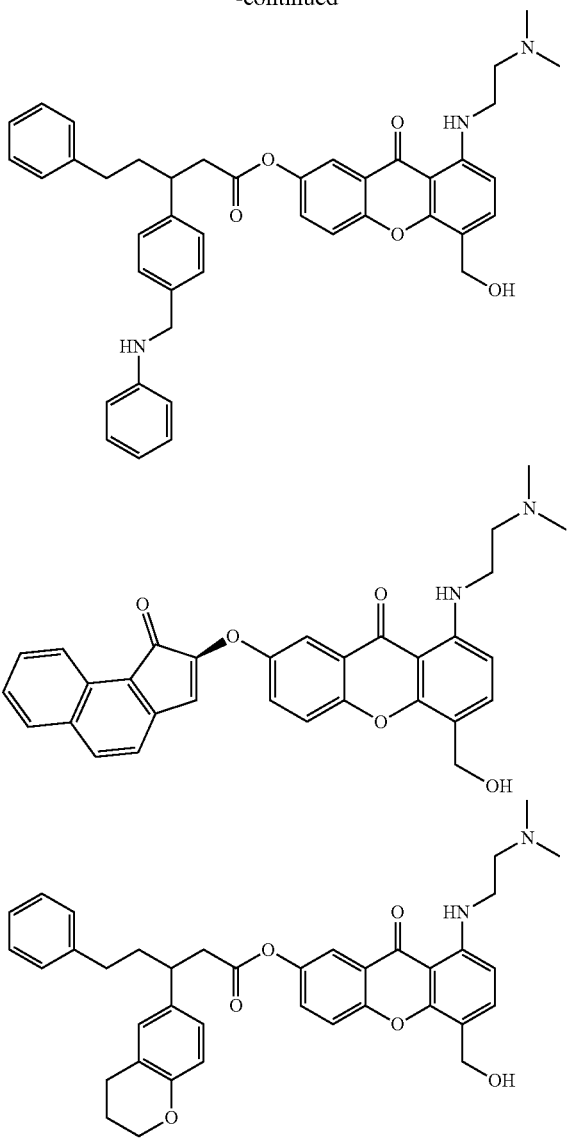

Kulemina and Ostrov describe further numerous ACE2 activators (Journal of Biomolecular Screening 2011; 16:878-885). a small molecule library of 139,735 compounds (molecular weight less than 500 da) from national Cancer institute (nCi) developmental therapeutics program plated set collection was docked into the selected site 1 and scored using an in silico grid-based scoring system. The highest scoring compounds were obtained and assayed in vitro for their abilities to enhance aCe2 catalytic activity. one of the compounds, [8-(2-dimethylaminoethylamino)-5-(hydroxymethyl)-9-oxoxanthen-2-yl]4-methyl-benzenesulfonate (from here on referred to as XNT) was shown to enhance the rate of catalysis by increasing the velocity of the enzyme approximately twofold. Because the molecular docking selection strategy was useful in identifying compounds that enhance ACE2 catalytic activity, a selection strategy was applied to a chemical library of 1217 food and drug administration (FDA)approved compounds.

ACE2 enzyme kinetic assays were carried out, by which the effects of 40 top-scoring compounds selected in virtual screening were tested in fluorescence-based kinetic assays using recombinant human enzyme and fluorogenic peptide substrate. Kinetic parameters for ACE2 in the presence of selected compounds were determined under steady-state conditions in the presence of saturating amounts of the substrate. Enzyme concentration was adjusted to ensure that <15% of the substrate was consumed at the lowest substrate concentration and product formation was linear with time. ACE2 assays for catalytic activity were carried out in a total volume of 100 µl, containing 75 mm tris-HCl (ph 7.4), 0.1m NaCl, 0.5 µm ZnCl2, 10 nm ACE2, and 0.01% triton-X. Small-molecule stocks were prepared by dissolving the compounds in DMSO to a concentration of 50 to 100 mm; a final concentration of 50 µm was used in all screening experiments. Compounds were preincubated in black 96-well plates with 10 nm human recombinant ACE2 (Enzo life sciences, Plymouth meeting, PA) for 15 min at 37° C. Reactions were initiated by addition of 25 to 250 µm fluorogenic peptide substrate Mca-APK (Dnp)-OH (Anaspec, Fremont, Calif.) and monitored continuously for 30 min with spectra max gemini m5 fluorescence reader from molecular devices (Sunnyvale, Calif.; Aexcitation=325 nm, Remission=395 nm). Initial velocities of ACE2 in the absence and in presence of 50-µm compounds were determined by measuring an increase in fluorescence upon hydrolysis of the substrate.

The screen revealed a number of ACE2 activators, selected preferably from the following:

NSC 354677 (XNT)

1-[[2-d imethylamino)ethyl]amino]-4-(hydroxymethyl)-7-[[(4-methylphenyl) sulfonyl]oxy]-9h-xanthen-9-one

NSC 290956 (ESP)

8-[3-(2-chlorophenothiazin-10-yl)propyI]-4-thia-1,8-diazaspiro[4.5]decan-2-one hydrochloride

NSC 357775 (DMZ)

4-[2-(4-carbamimidoylphenyl) iminohydrazinyl]benzenecarboximidamide dihydrochloride

NSC 169188 (HXZ)

2-[2-[4-[(4-chlorophenyl)-phenylmethyl]piperazin-1-yl] ethoxy]ethanol

NSC 169899 (CTX)

(3Z)-3-(2-chlorothioxanthen-9-ylidene)-n,ndimethylpropan-1-amine hydrochloride

NSC 134434 (HCT)

1-(2-diethylaminoethylamino)-4-(hydroxymethyl)thioxanthen-9-one

NSC 293901 (FMB)

n-[4-chloro-2-[[methyl-(2-morpholin-4-yl-2-oxoethyl) amino]methyl]phenyl]benzamide hydrochloride

NSC 289337 (TIA)

5-chloro-3-[2-[4-(2-hydroxyethyl)piperazin-1-yl]-2-oxoethyl]-1, 3-benzothiazol-2-one hydrochloride

NSC 284614 (APR)

n'-(2,3-dihydro-1h-inden-2-yl)-n,n-diethyl-n'-phenylpropane-1,3-diamine hydrochloride

NSC 290312 (LAB)

2-hydroxy-5[-hydroxy-2-(4-phenylbutan-2-ylamino)ethypenzamide hydrochloride

Shenoy et al (Am J Respir Crit Care Med Vol 187, Iss. 6, pp 648-657, Mar. 15, 2013) describe an antitrypanosomal drug, diminazene aceturate (DIZE; 4-[2-(4-carbamimidoylphenyl) iminohydrazinyl]benzenecarboximidamide dihydrochloride), to enhance the enzymatic activity of ACE2 in vitro and in vivo.

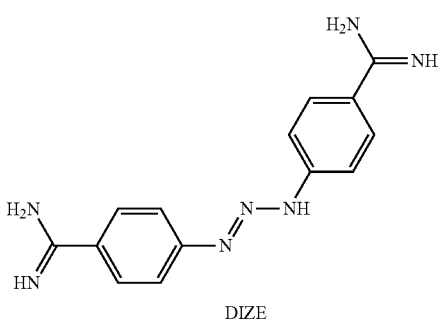 [SMILES: N=C(N)c1ccc(/N=N/Nc2ccc(C(=N)N)cc2)cc1]

DIZE

ACE2 peptides or variants thereof are also known to enhance ACE2 activity (EP 2332582, WO 2018/140456), which are hereby incorporated by reference.

Administration:

In a preferred embodiment, the administration occurs via topical administration, for example to the skin, or other surface of the body. This embodiment relates for example to either a medical or a non-medical use.

The present invention relates further to pharmaceutically acceptable salts of the compounds described herein. The term "pharmaceutically acceptable salt" refers to salts or esters of the compounds described herein prepared by conventional means that include basic salts of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. Any chemical compound recited in this specification may alternatively be administered as a pharmaceutically acceptable salt thereof. Also included are acidic salts of inorganic and organic bases, including but not limited to sodium, potassium, ammonium, triethylamine and the like.

"Pharmaceutically acceptable salts" are also inclusive of the free acid, base, and zwitterionic forms. Descriptions of suitable pharmaceutically acceptable salts can be found in Handbook of Pharmaceutical Salts, Properties, Selection and Use, Wiley VCH (2002). For therapeutic use, salts of the compounds are those wherein the counter-ion is pharmaceutically acceptable. However, salts of acids and bases which are non-pharmaceutically acceptable may also find use, for example, in the preparation or purification of a pharmaceutically acceptable compound.

Another aspect of the disclosure includes compositions prepared for administration to a subject and which include a therapeutically effective amount of one or more of the compounds disclosed herein. The therapeutically effective amount of a disclosed compound will depend on the route of administration, the species of subject and the physical characteristics of the subject being treated. Specific factors that can be taken into account include disease severity and stage, weight, diet and concurrent medications. The relationship of these factors to determining a therapeutically effective amount of the disclosed compounds is understood by those of skill in the art.

Compositions for administration to a subject can include at least one further pharmaceutically acceptable additive such as carriers, thickeners, diluents, buffers, preservatives, surface active agents and the like in addition to the molecule of choice. Pharmaceutical compositions can also include one or more additional active ingredients such as antimicrobial agents, anti-inflammatory agents, anesthetics, and the like. The pharmaceutically acceptable carriers useful for these formulations are conventional. Remington's Pharmaceutical Sciences, by E. W. Martin, Mack Publishing Co., Easton, Pa., 19th Edition (1995), describes compositions and formulations suitable for pharmaceutical delivery of the compounds herein disclosed.

In general, the nature of the carrier will depend on the particular mode of administration being employed. For instance, parenteral formulations usually contain injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

The compositions can be administered to subjects by a variety of mucosal administration modes, including by oral, rectal, intraocular, intranasal, intrapulmonary, or transdermal delivery, or by topical delivery to other surfaces. Optionally, the compositions can be administered by non-mucosal routes, including by intramuscular, intraocular, subcutaneous, intravenous, intra-arterial, intra-articular, intraperitoneal, intrathecal, intracerebroventricular, or parenteral routes.

The compositions of the disclosure can alternatively contain as pharmaceutically acceptable carrier substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate. For solid compositions, conventional nontoxic pharmaceutically acceptable vehicles can be used which include, for example, pharmaceutical grades of mannitol, lactose, starch, magnesium stearate, sodium saccharin, talcum, cellulose, glucose, sucrose, magnesium carbonate, and the like.

In a preferred embodiment, the invention comprise the topical and/or local administration of a compound as described herein and/or a composition comprising a compound as described herein to a subject. The term "topical administration" refers to the delivery of a pharmacologically active agent to the skin or mucosa of a patient. Topical administration can provide a local rather than a systemic effect. The terms "topical administration" and "transdermal administration" are used interchangeably to mean administration of a pharmacologically active agent to the skin or mucosa of a patient to achieve a therapeutic effect in treating or preventing the inflammatory skin disease at the site of topical or transdermal administration. Preferred administration modes relate to a topical solution, lotion, shake lotion, cream, ointment, gel, foam, transdermal patch, powder, solid form, sponge, tape, paste, make-up, foundation, pigmentation blocking make-up or tincture. Preferred embodiments relate to creams, foams, gels, lotions, make-up and ointments.

Various additives, known to those skilled in the art, may be included in topical compositions of the present disclosure. For example, solvents, including relatively small amounts of alcohol, may be used to solubilize a compound of the invention. Other optional additives include antioxidants, fragrances, colorant, gelling agents, emulsifiers, thickening agents, stabilizers, surfactants, buffers, cooling agents (e.g., menthol) and the like. Other agents may also be added, such as antimicrobial agents, to prevent spoilage upon storage, i.e., to inhibit growth of microbes such as yeasts and molds. Examples of suitable antimicrobial agents include methyl and propyl esters of p-hydroxybenzoic acid (i.e., methyl and propyl paraben), sodium benzoate, sorbic acid, imidurea, and the like. When applied to skin, a topical composition of the present disclosure can be covered with an occlusive or non-occlusive dressing, which may be porous or non-porous, so as to protect the composition from mechanical removal during the period of treatment, e.g. a plastic film food wrap or other non-absorbent film. Various inert coverings may be employed. Non-woven or woven coverings may be employed, particularly elastomeric coverings, which allow for heat and vapor transport. These coverings can allow for cooling of the pain site, which can provide for greater comfort, while protecting the composition from mechanical removal.

Compositions of the present disclosure can be included in a skin-contacting plaster or patch, i.e., a transdermal system, wherein the composition is contained within a material, e.g., a drug reservoir layer, that can be affixed to the skin. In certain embodiments, the active agent or agents can be contained in a drug reservoir layer underlying an upper backing layer. The system may contain a single reservoir, or it may contain multiple reservoirs. In these systems the active agent(s) may be formulated with the adhesive used to adhere the system to the skin. The system can include a backing layer which functions as the primary structural element of the transdermal system and can provide the system with flexibility and, preferably, occlusivity. The material used for the backing layer can be inert and incapable of absorbing the components of the composition contained within the system.

In accordance with the various treatment methods of the disclosure, the compound can be delivered to a subject in a manner consistent with conventional methodologies associated with management of the disorder for which treatment or prevention is sought. In accordance with the disclosure herein, a prophylactically or therapeutically effective amount of the compound and/or other biologically active agent is administered to a subject in need of such treatment for a time and under conditions sufficient to prevent, inhibit, and/or ameliorate a selected disease or condition or one or more symptom(s) thereof.

"Administration of" and "administering a" compound should be understood to mean providing a compound, a prodrug of a compound, or a pharmaceutical composition as described herein. The compound or composition can be administered by another person to the subject (e.g., intravenously, gel, cream, spray) or it can be self-administered by the subject (e.g., tablets, gel, cream, spray).

Dosage can be varied by the attending clinician to maintain a desired concentration at a target site (for example, the lungs or systemic circulation). Higher or lower concentrations can be selected based on the mode of delivery, for example, trans-epidermal, rectal, oral, pulmonary, or intranasal delivery versus intravenous or subcutaneous delivery. Dosage can also be adjusted based on the release rate of the administered formulation, for example, of an intrapulmonary spray versus powder, sustained release oral versus injected particulate or transdermal delivery formulations, and so forth.

The present invention also relates to a method of treatment of subjects suffering from the various medical conditions disclosed herein. The method of treatment comprises preferably the administration of a therapeutically effective amount of a compound disclosed herein to a subject in need thereof.

A "therapeutically effective amount" refers to a quantity of a specified agent sufficient to achieve a desired effect in a subject being treated with that agent. For example, this may be the amount of a compound disclosed herein useful in alleviating pain in a subject. The therapeutically effective amount or diagnostically effective amount of an agent will be dependent on the subject being treated, the severity of the condition, and the manner of administration of the therapeutic composition.

Dosage regimens can be adjusted to provide an optimum prophylactic or therapeutic response. A therapeutically effective amount is also one in which any toxic or detrimental side effects of the compound and/or other biologically active agent is outweighed in clinical terms by therapeutically beneficial effects. A non-limiting range for a therapeutically effective amount of a compound and/or other biologically active agent within the methods and formulations of the disclosure is about 0.001 mg/kg body weight to 50 mg/kg body weight, 0.01 mg/kg body weight to about 20 mg/kg body weight, such as about 0.05 mg kg to about 5 mg/kg body weight, or about 0.2 mg/kg to about 2 mg/kg body weight.

The instant disclosure also includes kits, packages and multi-container units containing the herein described compositions, active ingredients, and/or means for administering the same for use in the prevention and treatment of diseases and other non-medical conditions in mammalian subjects.

The present invention is further described by reference to the following non-limiting figures and examples.

FIGURES

The invention is further described by the following figures. These are not intended to limit the scope of the invention, but represent preferred embodiments of aspects of the invention provided for greater illustration of the invention described herein.

FIG. 1: Melanogenesis gene expression in the skin of ACE-KO mice on FVB/N and C57131/6 genetic background compared to respective controls (upper panels) and coat colour of ACE2-knockout mice on FVB/N genetic background (upper group; lower group: FVB/N controls) (lower panel).

Figure 2:
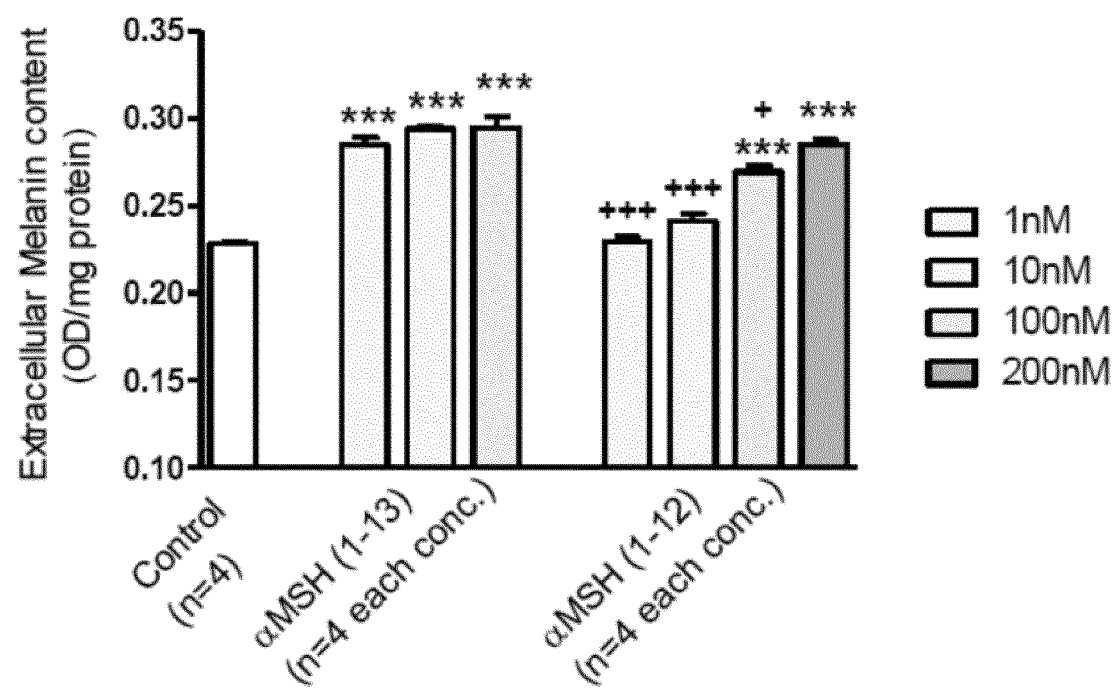

FIG. 2: Melanogenesis in B16F10 melanoma cells stimulated with $\alpha$-MSH$_{1-13}$ and $\alpha$-MSH$_{1-12}$. *** $p<0.001$ compared to control without $\alpha$-MSH, +++, $+p<0.001$, $p<0.05$ $\alpha$-MSH$_{1-12}$ compared to the same concentration of $\alpha$-MSH$_{1-13}$.

Figure 3:
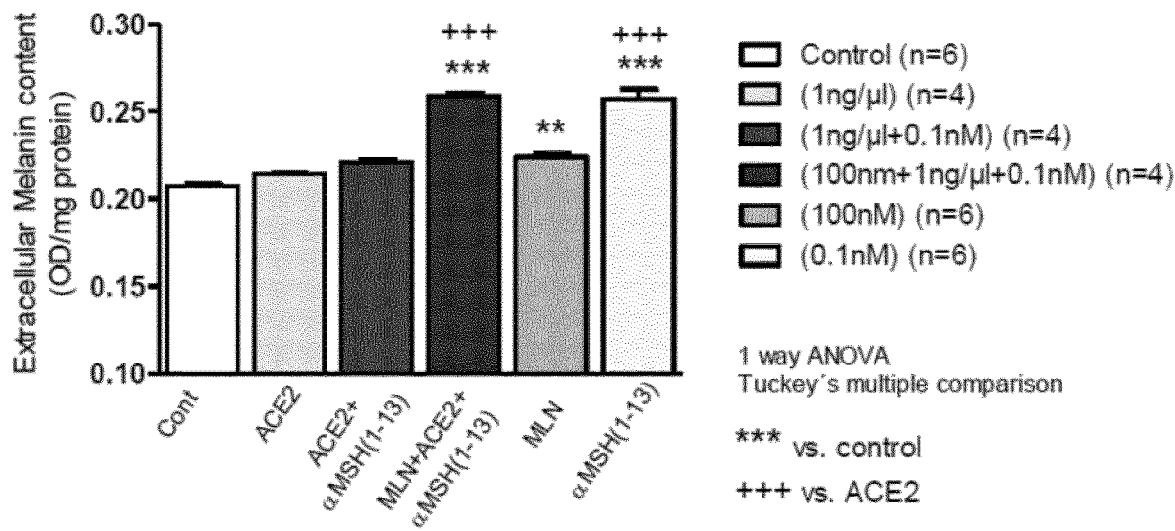
Figure 3:
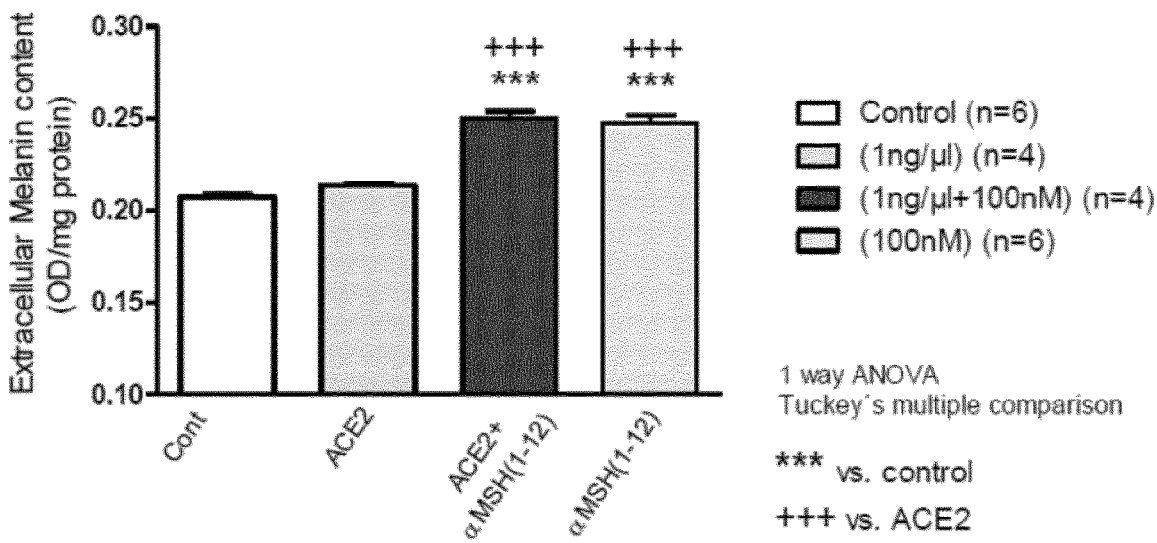

FIG. 3: Inhibition of the melanogenic effect of $\alpha$-MSH$_{1-13}$ (upper panel), but not of $\alpha$-MSH$_{1-12}$ (lower panel), by human recombinant ACE2 in B16F10 melanoma cells. The specific ACE2-inhibitor MLN-4760 inhibits the effect of ACE2. , $p<0.01$; *, $+++p<0.001$ FIG. 4: ACE2 limits the efficiency of $\alpha$MSH$_{1-13}$ in human skin; Tyrosinase expression. Tyrosinase (melanin synthesizing enzyme) mRNA expression was measured in human abdominal skin biopsies after treatment with vehicle, 10 nM $\alpha$MSH$_{1-13}$, 10 nM $\alpha$MSH$_{1-13}$+100 nM of the ACE2-Inhibitor MLN4760, or 100 nM MLN4760 alone. As expected, $\alpha$MSH$_{1-13}$ stimulates tyrosinase expression. This effect is increased by ACE2 inhibition. ACE2 inhibition alone already stimulates tyrosinase expression. These results indicate that ACE2 limits the efficiency of αMSH$_{1-13}$ in human skin. *p<0.05.

Figure 5:
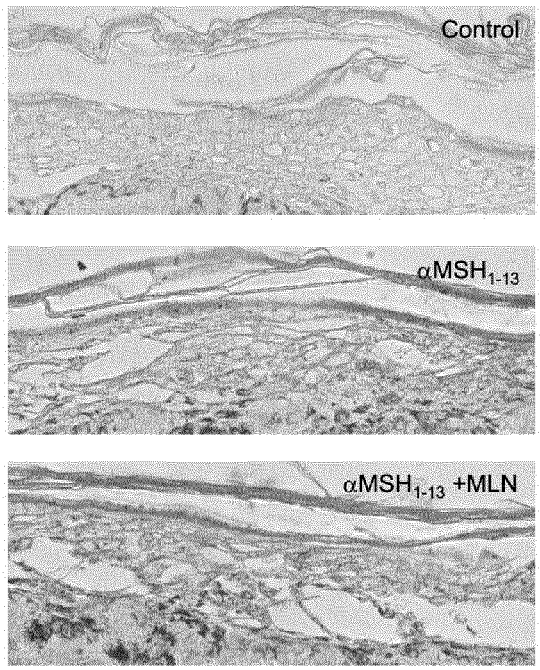

FIG. 5: ACE2 limits the efficiency of αMSH$_{1-13}$ in human skin; Fontana-Masson staining in human abdominal skin biopsies. Melanin was stained black by Fontana-Masson staining in human abdominal skin biopsies after treatment with vehicle, 10 nM αMSH$_{1-13}$, or 10 nM αMSH$_{1-13}$+100 nM of the ACE2-Inhibitor MLN476. As expected, αMSH$_{1-13}$ increases melanin levels. This effect is further increased by ACE2 inhibition. These results again indicate that ACE2 limits the efficiency of αMSH$_{1-13}$ in human skin.

Figure 6:
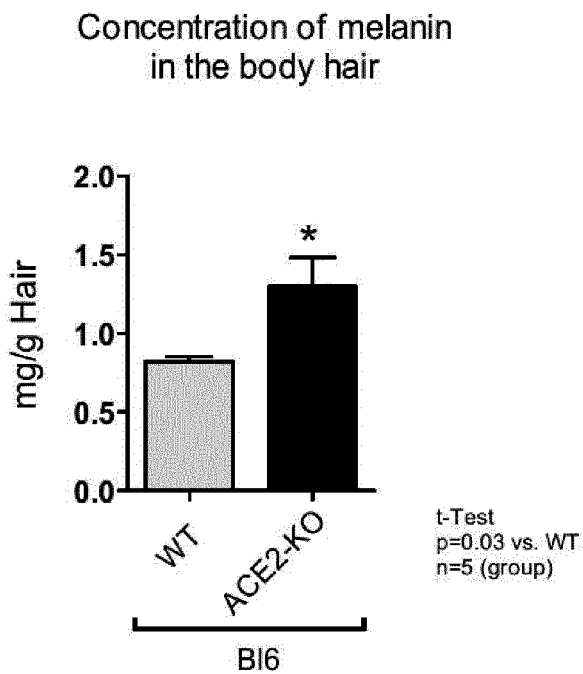

FIG. 6: ACE2 plays a limiting role on melanin synthesis in mouse skin. Melanin was isolated from hair of C57131/6 (B16) wildtype (WT) and ACE2-deficient (KO) mice and quantified by spectrophotometry (405 nm). The melanin content is higher in the absence of ACE2 confirming a limiting role of ACE2 on melanin synthesis in mouse skin. *p<0.05.

Figure 7:
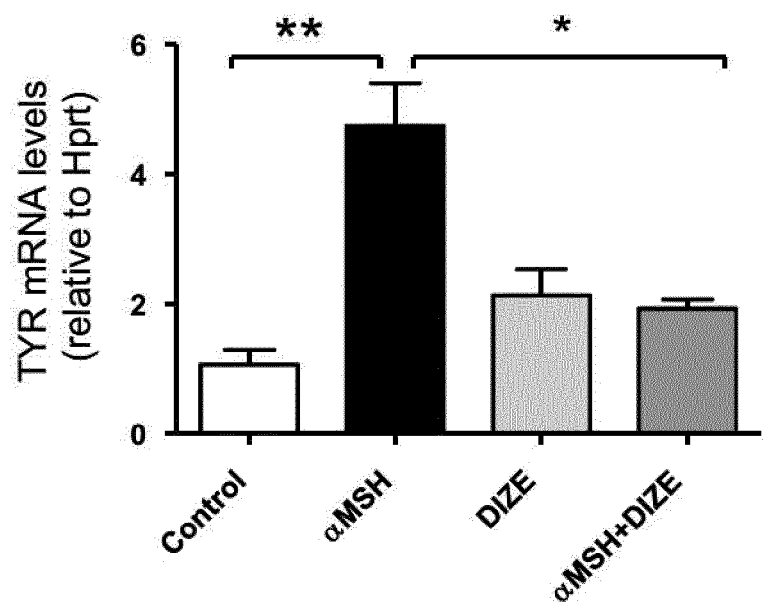

FIG. 7: DIZE inhibits the stimulating effect of aMSH by activating ACE2 or increasing its expression. B16F10 mouse melanoma cells were incubated with 1 nM aMSH, 10 ng/μl diminazene aceturate (DIZE, ACE2 activator) or a combination of both for 48 hours and the expression of the melanin-synthesizing enzyme tyrosinase (TYR) was quantified by real-time RT-PCR; **p<0.01; *p<0.05.

Figure 8:
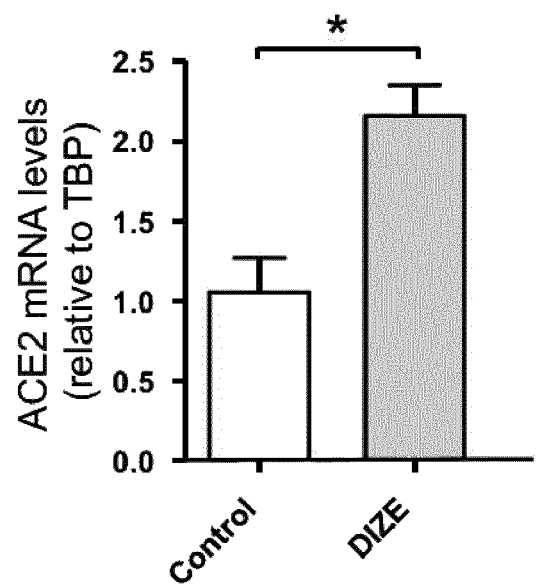

FIG. 8: DIZE stimulates ACE2 expression in B16F10 mouse melanoma cells. B16F10 mouse melanoma cells were incubated with 10 ng/μl diminazene aceturate (DIZE, ACE2 activator) for 48 hours and the expression of ACE2 was quantified by real-time RT-PCR; *p<0.05. DIZE stimulates ACE2 expression in these cells

EXAMPLES

The invention is further described by the following examples. These are not intended to limit the scope of the invention, but represent preferred embodiments of aspects of the invention provided for greater illustration of the invention described herein.

Generation and Characterisation of ACE2-KO mice

The inventors have investigated the renin-angiotensin system and in particular its protective arm. This arm comprises ACE2, generating the peptide angiotensin(1-7), which interacts with its receptor Mas to exert antihypertensive, antihypertrophic, and antiinflammatory actions in the cardiovascular system (Bader, 2013, Rentzsch et al., 2008).

Since also PRCP can generate angiotensin(1-7), the inventors generated and characterized besides ACE2-KO mice (Rabelo et al., 2016; Motta-Santos et al., 2016; Nunez-Souza et al., 2016) also mice lacking PRCP (Maier et al., 2017). These mice were used to analyze which enzyme may degrade α-MSH in the skin.

The inventors have found that the skin of ACE2-KO mice overexpresses several melanogenic genes, such a tyrosinase, Trp1, Trp2 and GPNMB, compared to the skin of control mice (FIG. 1). Accordingly, ACE2-KO mice on an albino background (FVB/N) were not completely white as their controls but showed a cream coat colour (FIG. 1). These findings demonstrate that ACE2 degrades α-MSH, and that mice lacking the enzyme therefore exhibit increased skin concentrations of the peptide visualized by the increased melanogenic activity. This is also supported by the fact, that ACE2 is a carboxypeptidase preferentially cutting peptide substrates with a proline residue at the penultimate position (Vickers et al., 2002), as it is the case for α-MSH.

The inventors have shown that the expected ACE2 digestion product of α-MSH1-13, α-MSH1-12, is at least 100 times less active in a cell culture assay for melanogenesis using B16F10 mouse melanoma cells (FIG. 2).

Additionally, the inventors could verify that the addition of human recombinant ACE2 to α-MSH1-13, but not to α-MSH1-12, reduces its melanogenic activity in this cell culture model (FIG. 3). In wild-type mice, the inventors further confirmed previous studies in humans (Ham-ming et al., 2004, Grzegrzolka et al., 2013) showing that ACE2 is expressed in the skin.

It appears ACE2 directly degrades α-MSH ACE2. Not to be bound by theory, ACE2 may however not directly degrade α-MSH, but may only indirectly activate its action on melanocytes.

Figure 4:
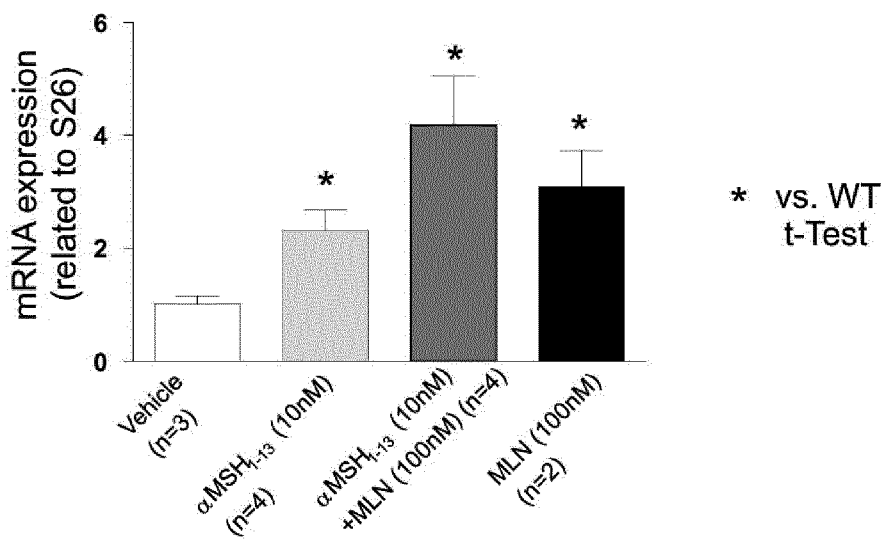

ACE2 Limits the Efficiency of αMSH1-13 in Human Skin:

As shown in FIGS. 4 and 5, Tyrosinase (melanin synthesizing enzyme) mRNA expression was measured in human abdominal skin biopsies, and Melanin was stained black by Fontana-Masson staining in human abdominal skin biopsies. Biopsies were treated with vehicle, 10 nM αMSH1-13, 10 nM αMSH1-13+100 nM of the ACE2-Inhibitor MLN4760, or 100 nM MLN4760 alone.

As expected, αMSH1-13 stimulates tyrosinase expression. This effect is increased by ACE2 inhibition. ACE2 inhibition alone already stimulates tyrosinase expression.

Also, as expected, αMSH1-13 increases melanin levels. This effect is further increased by ACE2 inhibition. These results again indicate that ACE2 limits the efficiency of αMSH1-13 in human skin.

ACE2 Plays a Limiting Role on Melanin Synthesis in Mouse Skin:

As shown in FIG. 6, Melanin was isolated from hair of C57131/6 (B16) wildtype (WT) and ACE2-deficient (KO) mice and quantified by spectrophotometry (405 nm). The melanin content is higher in the absence of ACE2 confirming a limiting role of ACE2 on melanin synthesis in mouse skin.

Further experimentation is ongoing to further support and elucidate the present invention.

DIZE Inhibits the Stimulating Effect of αMSH by Activating ACE2 or Increasing its Expression:

As shown in FIGS. 7 and 8, DIZE inhibits the stimulating effect of αMSH, probably by activating ACE2 or increasing its expression in B16F10 mouse melanoma cells. B16F10 mouse melanoma cells were incubated with 1 nM aMSH, 10 ng/μl diminazene aceturate (DIZE, ACE2 activator) or a combination of both for 48 hours and the expression of the melanin-synthesizing enzyme tyrosinase (TYR) was quantified by real-time RT-PCR. DIZE inhibits the stimulating effect of αMSH.

Furthermore, B16F10 mouse melanoma cells were incubated with 10 ng/μl diminazene aceturate (DIZE, ACE2 activator) for 48 hours and the expression of ACE2 was quantified by real-time RT-PCR. DIZE stimulates ACE2 expression in these cells.

We further expect XNT to provide a similar effect in assays of this kind.

Measurement of α-MSH and Degradation Products in the Skin of ACE2-KO, PRCP-KO, and Wild-Type Mice by LC-MS:

An LC/MS method is carried out to distinguish between α-MSH$_{1-13}$ and α-MSH$_{1-12}$, the putative degradation product generated by ACE2. Skin and other organs of ACE2-KO, PRCP-KO and wild-type mice are isolated and the content of these peptides is measured. Degradation may be performed with or without an agent of the invention (ACE2 modulator). We expect to observe degradation of alpha MSH by ACE2 incubation, and subsequent inhibition or activation of this activity in the presence of ACE2 inhibitors or activators, respectively.

α-MSH Degradation Studies in vitro:

$MSH_{1-13}$ is incubated with commercially available recombinant human ACE2 and the resulting products are analyzed by LC/MS. Degradation may be performed with or without an agent of the invention (ACE2 modulator). We expect to observe degradation of alpha MSH by ACE2 incubation, and subsequent inhibition or activation of this activity in the presence of ACE2 inhibitors, or activators, respectively.

Effect of ACE2 Inhibition on Skin and Hair Pigmentation in vivo:

Agouti-coloured wild-type and ACE2-KO mice are partially shaved and the ACE2 inhibitor, MLN-4760 ($IC_{50}$: 0.5 nM), is applied to the skin at a 10 mM concentration for 3 consecutive days. Then some animals are sacrificed and the concentration of α-$MSH_{1-13}$ and α-$MSH_{1-12}$ and the expression of melanogenesis genes is determined at the site of application and compared to another untreated part of the skin. Some animals remain alive and the colour of the regrown hair is determined.

Incubation of Human Skin Biopsies with ACE2 Activators (E.G., DIZE) in Tissue Culture Inhibits Melanin Synthesis and Reduces Melanin Content:

Human abdominal skin biopsies are commercially available. They will be incubated for 5 days with 3 different concentrations of the ACE2 activator diminazene aceturate (DIZE) or XNT. For each concentration 6 different skin discs will be applied. Afterwards, the skin samples will be cut in 2 pieces and melanin content will be measured in one part by a spectrophotometric method. For this purpose, the tissue will be powdered in liquid nitrogen and then incubated in 1 M NaOH and 10% DMSO for 24 h. After centrifugation the melanin content will be measured using an absorbance reader at 475 nm and normalized to the total tissue protein concentration. Moreover, expression of melanogenesis genes, such as for tyrosinase, Trp1, and Trp2, will be quantified by real-time qPCR in RNA isolated from the other part of the skin samples. We expect a dose-dependent decrease in melanin content and melanogenesis gene expression by DIZE or XNT treatment.

Injection of ACE2 Inhibitors (E.G., MLN4760) into Mice Stimulates Melanin Synthesis in the Skin and Increases Melanin Content:

The ACE2 inhibitor MLN4760 will be injected into the skin of mice at 3 different concentrations daily for 4 days. Afterwards the skin is isolated and cut in 2 pieces. Melanin content will be measured in one part by a spectrophotometric method. For this purpose, the tissue will be powdered in liquid nitrogen and then incubated in 1 M NaOH and 10% DMSO for 24 h. After centrifugation the melanin content will be measured using an absorbance reader at 475 nm and normalized to the total tissue protein concentration. Moreover, expression of melanogenesis genes, such as for tyrosinase, Trp1, and Trp2, will be quantified by real-time qPCR in RNA isolated from the other part of the skin samples. We expect a dose-dependent increase in melanin content and melanogenesis gene expression by MLN4760 treatment.

Injection of ACE2 Activators (e.g., DIZE) into Mice Inhibits Melanin Synthesis in the Skin and Reduces Melanin Content:

The ACE2 activator DIZE or XNT will be injected into the skin of mice at 3 different concentrations daily for 4 days. Afterwards the skin is isolated and cut in 2 pieces. Melanin content will be measured in one part by a spectrophotometric method. For this purpose, the tissue will be powdered in liquid nitrogen and then incubated in 1 M NaOH and 10% DMSO for 24 h. After centrifugation the melanin content will be measured using an absorbance reader at 475 nm and normalized to the total tissue protein concentration. Moreover, expression of melanogenesis genes, such as for tyrosinase, Trp1, and Trp2, will be quantified by real-time qPCR in RNA isolated from the other part of the skin samples. We expect a dose-dependent decrease in melanin content and melanogenesis gene expression by DIZE or XNT treatment.

Topical Application of ACE2 Inhibitors (E.G., MLN4760) to the Skin of Mice and Human Volunteers Stimulates Melanin Synthesis, Increases Melanin Levels, and Tans the Skin:

The ACE2 inhibitor MLN4760 will be topically applied to the skin of C57BL/6 mice at 3 different concentrations daily for 4 days. Afterwards the skin is isolated and cut in 2 pieces. Melanin content will be measured in one part by a spectrophotometric method. For this purpose, the tissue will be powdered in liquid nitrogen and then incubated in 1 M NaOH and 10% DMSO for 24 h. After centrifugation the melanin content will be measured using an absorbance reader at 475 nm and normalized to the total tissue protein concentration. Moreover, expression of melanogenesis genes, such as for tyrosinase, Trp1, and Trp2, will be quantified by real-time qPCR in RNA isolated from the other part of the skin samples. We expect a dose-dependent increase in melanin content and melanogenesis gene expression by MLN4760 treatment.

The ACE2 inhibitor MLN4760 will be topically applied to the skin of Caucasian volunteers at 3 different concentrations daily for 4 days. Afterwards the skin pigmentation is quantified by a Skin Pigmentation Analyzer. We expect a dose-dependent increase in skin pigmentation by MLN4760 treatment.

Topical Application of ACE2 Activators (E.G., DIZE) to the Skin of Mice and Human Volunteers Inhibits Melanin Synthesis, Reduces Melanin Levels, and Lightens The Skin:

The ACE2 activator DIZE or XNT will be topically applied to the skin of C57BL/6 mice at 3 different concentrations daily for 4 days. Afterwards the skin is isolated and cut in 2 pieces. Melanin content will be measured in one part by a spectrophotometric method. For this purpose, the tissue will be powdered in liquid nitrogen and then incubated in 1 M NaOH and 10% DMSO for 24 h. After centrifugation the melanin content will be measured using an absorbance reader at 475 nm and normalized to the total tissue protein concentration. Moreover, expression of melanogenesis genes, such as for tyrosinase, Trp1, and Trp2, will be quantified by real-time qPCR in RNA isolated from the other part of the skin samples. We expect a dose-dependent decrease in melanin content and melanogenesis gene expression by DIZE or XNT treatment.

The ACE2 activator MLN4760 will be topically applied to the skin of Caucasian volunteers at 3 different concentrations daily for 4 days. Afterwards the skin pigmentation is quantified by a Skin Pigmentation Analyzer. We expect a dose-dependent decrease in skin pigmentation by DIZE treatment.

REFERENCES

Abdel-Malek Z A, Swope V B, Starner R J, Koikov L, Cassidy P, Leachman S. Melanocortins and the melanocortin 1 receptor, moving translationally towards melanoma prevention. Arch Biochem Biophys. 2014; 563:4-12

Bader M. ACE2, Angiotensin-(1-7), and Mas: The other side of the coin. Pflugers Arch. 2013, 465: 79-85.

Biba E. Protection: the sunscreen pill. Nature. 2014 Nov. 20; 515(7527):S124-5

Cahn A, Cernea S, Raz I. An update on DPP-4 inhibitors in the management of type 2 diabetes. Expert Opin Emerg Drugs. 2016 December; 21(4):409-419

Campbell D J. Long-term neprilysin inhibition—implications for ARNIs. Nat Rev Cardiol. 2017 March; 14(3): 171-186

Dales N A, Gould A E, Brown J A, Calderwood E F, Guan B, Minor C A, Gavin J M, Hales P, Kaushik V K, Stewart M, Tummino P J, Vickers C S, Ocain T D, Patane M A. Substrate-based design of the first class of angiotensin-converting enzyme-related carboxypeptidase (ACE2) inhibitors. J Am Chem Soc. 2002 October 9; 124(40): 11852-3

Ericson M D, Lensing C J, Fleming K A, Schlasner K N, Doering S R, Haskell-Luevano C. Bench-top to clinical therapies: A review of melanocortin ligands from 1954 to 2016. Biochim Biophys Acta. 2017 March 29. pii: S0925-4439(17)30107-2.

Grzegrzolka J, Swiatko K, Pula B, Zamirska A, Olbromski M, Bieniek A, Szepietowski J, Rys J, Dziegiel P, Podhorska-Okolow M. ACE and ACE2 expression in normal and malignant skin lesions. Folia Histochem Cytobiol. 2013; 51(3):232-8.

Hamming I, Timens W, Bulthuis M L, Lely A T, Navis G, van Goor H. Tissue distribution of ACE2 protein, the functional receptor for SARS coronavirus. A first step in understanding SARS pathogenesis. J Pathol. 2004; 203: 631-7.

Herpin T F, Yu G, Carlson K E, Morton G C, Wu X, Kang L, Tuerdi H, Khanna A, Tokarski J S, Lawrence R M, Macor J E. Discovery of tyrosine-based potent and selective melanocortin-1 receptor small-molecule agonists with anti-inflammatory properties. J Med Chem. 2003 March 27; 46(7):1123-6.

Huang L, Sexton D J, Skogerson K, Devlin M, Smith R, Sanyal I, Parry T, Kent R, Enright J, Wu Q L, Conley G, DeOliveira D, Morganelli L, Ducar M, Wescott C R, Ladner R C. Novel peptide inhibitors of angiotensin-converting enzyme 2. J Biol Chem. 2003 May 2; 278(18): 15532-40.

Jeong J K, Diano S. Prolyl carboxypeptidase and its inhibitors in metabolism. Trends Endocrinol Metab. 2013; 24:61-7

Kang L, McIntyre K W, Gillooly K M, Yang Y, Haycock J, Roberts S, Khanna A, Herpin T F, Yu G, Wu X, Morton G C, Tuerdi H, Koplowitz B, Walker S G, Wardwell-Swanson J, Macor J E, Lawrence R M, Carlson K E. A selective small molecule agonist of the melanocortin-1 receptor inhibits lipopolysaccharide-induced cytokine accumulation and leukocyte infiltration in mice. J Leukoc Biol. 2006 October; 80(4):897-904

Lindskog Jonsson A, Granqvist A, Elvin J, Johansson M E, Haraldsson B, Nystrom J. Effects of melanocortin 1 receptor agonists in experimental nephropathies. PLoS One. 2014 January 30; 9(1):e87816

Maier C, Schadock I, Haber P K, Wysocki J, Ye M, Kanwar Y, Flask C A, Yu X, Hoit B D, Adams G N, Schmaier A H, Bader M, Bathe D. Prolylcarboxypeptidase deficiency is associated with increased blood pressure, glomerular lesions, and cardiac dysfunction independent of altered circulating and cardiac angiotensin II. J Mol Med (Berl) 2017, 95(5):473-486

Minder El, Barman-Aksoezen J, Schneider-Yin X. Pharmacokinetics and Pharmacodynamics of Afamelanotide and its Clinical Use in Treating Dermatologic Disorders. Clin Pharmacokinet. 2017 January 6. doi: 10.1007/s40262-016-0501-5.

Motta-Santos D, Dos Santos R A, Oliveira M, Qadri F, Poglitsch M, Mosienko V, Kappes B L, Campagnole-Santos M J, Penninger M, Alenina N, Bader M. Effects of ACE2 deficiency on physical performance and physiological adaptations of cardiac and skeletal muscle to exercise. Hypertens Res 2016; 39:506-512

Nunes-Souza V, Alenina N, Qadri F, Penninger J M, Santos R A, Bader M, Rabelo L A. CD36/Sirtuin 1 Axis Impairment Contributes to Hepatic Steatosis in ACE2-Deficient Mice. Oxid Med Cell Longev 2016; 2016:6487509.

Paus R. A neuroendocrinological perspective on human hair follicle pigmentation. Pigment Cell Melanoma Res. 2011 February; 24(1):89-106.

Rabelo L A, Todiras M, Nunes-Souza V, Qadri F, Szijarto I A, Gollasch M, Penninger J M, Bader M, Santos R A, Alenina N. Genetic Deletion of ACE2 Induces Vascular Dysfunction in C57BL/6 Mice: Role of Nitric Oxide Imbalance and Oxidative Stress. PLoS One 2016; 11:e0150255

Rentzsch B, Todiras M, Iliescu R, Popova E, Campos L A, Oliveira M L, Baltatu O C, Santos R A, Bader M. Transgenic ACE2 overexpression in vessels of SHRSP rats reduces blood pressure and improves endothelial function. Hypertension. 2008, 52:967-97

Shah P P, Desai P R, Boakye C H, Patlolla R, Kikwai L C, Babu R J, Singh M. Percutaneous delivery of α-melanocyte-stimulating hormone for the treatment of imiquimod-induced psoriasis. J Drug Target. 2016; 24(6):537-47

Vickers C, Hales P, Kaushik V, Dick L, Gavin J, Tang J, Godbout K, Parsons T, Baronas E, Hsieh F, Acton S, Patane M, Nichols A, Tummino P. Hydrolysis of biological peptides by human angiotensin-converting enzyme-related carboxypeptidase. J Biol Chem. 2002 April 26; 277(17):14838-43.

Wallingford N, Perroud B, Gao Q, Coppola A, Gyengesi E, Liu Z W, Gao X B, Diament A, Haus K A, Shariat-Madar Z, Mandi F, Wardlaw S L, Schmaier A H, Warden C H, Diano S. Prolylcarboxypeptidase regulates food intake by inactivating alpha-MSH in rodents. J Clin Invest. 2009 August; 119(8):2291-303

The invention claimed is:

1. A method for the treatment of an inflammatory skin disease, the method comprising administering an inhibitor of angiotensin-converting enzyme 2 (ACE2 inhibitor) to a subject in need thereof.

2. The method according to claim 1, wherein the ACE2 inhibitor inhibits the carboxypeptidase digestion of α-melanocyte stimulating hormone (α-MSH).

3. The method according to claim 1, wherein the ACE2 inhibitor leads to one or more effects selected from the group consisting of:
elevated levels of α-$MSH_{1-13}$ in subjects who have received ACE2 inhibitor treatment compared to subjects who have not received said treatment,
elevated levels of one or more melanins in subjects who have received ACE2 inhibitor treatment compared to subjects who have not received said treatment, and
elevated expression of one or more melanogenic genes in subjects who have received ACE2 inhibitor treatment compared to subjects who have not received said treatment.

4. The method according to claim 1, wherein the inflammatory skin disease is selected from the group consisting of protoporphyria, psoriasis, vitiligo, acne, solar urticaria (SU), Hailey-Hailey disease, Polymorphous light eruption (PLE), alopecia areata and overexposure of skin to ultraviolet (UV) radiation (sun burn).

5. The method according to claim 1, wherein the treatment reduces the risk of a subject to overexposure of the skin to ultraviolet (UV) radiation (sun burn).

6. The method according to claim 1, wherein the treatment reduces the risk of a subject to melanoma.

7. The method according to claim 1, wherein the ACE2 inhibitor is administered topically.

8. The method of claim 4, wherein the protoporphyria is erythropoietic protoporphyria (EPP).

* * * * *

SEQUENCE LISTING

<160> NUMBER OF SEQ ID NOS: 23

<210> SEQ ID NO 1
<211> LENGTH: 21
<212> TYPE: PRT
<213> ORGANISM: Artificial Sequence
<220> FEATURE:
<223> OTHER INFORMATION: Synthetic peptide

<400> SEQUENCE: 1

Gly Ser Asn Arg Glu Cys His Ala Leu Phe Cys Met Asp Phe Ala Pro
1               5                   10                  15

Gly Glu Gly Gly Gly
            20

<210> SEQ ID NO 2
<211> LENGTH: 21
<212> TYPE: PRT
<213> ORGANISM: Artificial Sequence
<220> FEATURE:
<223> OTHER INFORMATION: Synthetic peptide

<400> SEQUENCE: 2

Gly Ser Ser Pro Thr Cys Arg Ala Leu Phe Cys Val Asp Phe Ala Pro
1               5                   10                  15

Gly Glu Gly Gly Gly
            20

<210> SEQ ID NO 3
<211> LENGTH: 21
<212> TYPE: PRT
<213> ORGANISM: Artificial Sequence
<220> FEATURE:
<223> OTHER INFORMATION: Synthetic peptide

<400> SEQUENCE: 3

Gly Ser Leu Glu Met Cys Glu Ala Leu Phe Cys Val Glu Phe Ala Pro
1               5                   10                  15

Gly Glu Gly Gly Gly
            20

<210> SEQ ID NO 4
<211> LENGTH: 24
<212> TYPE: PRT
<213> ORGANISM: Artificial Sequence
<220> FEATURE:
<223> OTHER INFORMATION: Synthetic peptide

<400> SEQUENCE: 4

Gly Ser Asn Asp Tyr Cys Thr Val Phe Thr Gly Ala Leu Phe Cys Leu
1               5                   10                  15

Asp Phe Ala Pro Glu Gly Gly Gly
            20

<210> SEQ ID NO 5
<211> LENGTH: 25
<212> TYPE: PRT
<213> ORGANISM: Artificial Sequence
<220> FEATURE:
<223> OTHER INFORMATION: Synthetic peptide

<400> SEQUENCE: 5

Gly Ser Pro Asn Gln Cys Gly Val Asp Ile Trp Ala Leu Phe Cys Val
1               5                   10                  15

Asp Phe Ala Pro Glu Gly Gly Gly Lys
            20                  25

<210> SEQ ID NO 6
<211> LENGTH: 22
<212> TYPE: PRT
<213> ORGANISM: Artificial Sequence
<220> FEATURE:

<223> OTHER INFORMATION: Synthetic peptide

<400> SEQUENCE: 6

Ala Gly Glu Gly Asn Cys Phe Leu Ile Gly Pro Trp Cys Phe Glu Phe
1               5                   10                  15

Gly Thr Glu Gly Gly Gly
            20

<210> SEQ ID NO 7
<211> LENGTH: 24
<212> TYPE: PRT
<213> ORGANISM: Artificial Sequence
<220> FEATURE:
<223> OTHER INFORMATION: Synthetic peptide

<400> SEQUENCE: 7

Gly Ser Tyr Asp Asn Cys Leu Gly Leu Ala Asn Leu Asn Phe Cys Phe
1               5                   10                  15

Asp Phe Ala Pro Glu Gly Gly Gly
            20

<210> SEQ ID NO 8
<211> LENGTH: 26
<212> TYPE: PRT
<213> ORGANISM: Artificial Sequence
<220> FEATURE:
<223> OTHER INFORMATION: Synthetic peptide

<400> SEQUENCE: 8

Gly Asp Asp Asp Cys Gly Trp Ile Gly Phe Ala Asn Phe His Leu
1               5                   10                  15

Cys Leu His Gly Asp Pro Glu Gly Gly Gly
            20                  25

<210> SEQ ID NO 9
<211> LENGTH: 26
<212> TYPE: PRT
<213> ORGANISM: Artificial Sequence
<220> FEATURE:
<223> OTHER INFORMATION: Synthetic peptide

<400> SEQUENCE: 9

Gly Asp Pro Phe Glu Cys Asp Trp Gly Pro Trp Thr Leu Glu Met Leu
1               5                   10                  15

Cys Gly Pro Pro Asp Pro Glu Gly Gly Gly
            20                  25

<210> SEQ ID NO 10
<211> LENGTH: 21
<212> TYPE: PRT
<213> ORGANISM: Artificial Sequence
<220> FEATURE:
<223> OTHER INFORMATION: Synthetic peptide

<400> SEQUENCE: 10

Gly Ser Arg Ile Gly Cys Arg Asp Ser Arg Cys Asn Trp Trp Ala Pro
1               5                   10                  15

Gly Glu Gly Gly Gly
            20

<210> SEQ ID NO 11
<211> LENGTH: 21
<212> TYPE: PRT
<213> ORGANISM: Artificial Sequence

```
<220> FEATURE:
<223> OTHER INFORMATION: Synthetic peptide

<400> SEQUENCE: 11

Gly Ser Arg Gly Phe Cys Arg Asp Ser Ser Cys Ser Phe Pro Ala Pro
1               5                   10                  15

Gly Glu Gly Gly Gly
            20

<210> SEQ ID NO 12
<211> LENGTH: 21
<212> TYPE: PRT
<213> ORGANISM: Artificial Sequence
<220> FEATURE:
<223> OTHER INFORMATION: Synthetic peptide

<400> SEQUENCE: 12

Gly Ser Trp Pro Thr Cys Leu Thr Met Asp Cys Val Tyr Asn Ala Pro
1               5                   10                  15

Gly Glu Gly Gly Gly
            20

<210> SEQ ID NO 13
<211> LENGTH: 21
<212> TYPE: PRT
<213> ORGANISM: Artificial Sequence
<220> FEATURE:
<223> OTHER INFORMATION: Synthetic peptide

<400> SEQUENCE: 13

Ala Gly Trp Val Leu Cys Phe Glu Trp Glu Asp Cys Asp Glu Lys Gly
1               5                   10                  15

Thr Glu Gly Gly Gly
            20

<210> SEQ ID NO 14
<211> LENGTH: 22
<212> TYPE: PRT
<213> ORGANISM: Artificial Sequence
<220> FEATURE:
<223> OTHER INFORMATION: Synthetic peptide

<400> SEQUENCE: 14

Ala Gly Val Tyr Phe Cys Phe Asp Trp Glu Gln Asp Cys Asp Glu Met
1               5                   10                  15

Gly Thr Glu Gly Gly Gly
            20

<210> SEQ ID NO 15
<211> LENGTH: 22
<212> TYPE: PRT
<213> ORGANISM: Artificial Sequence
<220> FEATURE:
<223> OTHER INFORMATION: Synthetic peptide

<400> SEQUENCE: 15

Ala Gly Trp Glu Val Cys His Trp Ala Pro Met Met Cys Lys His Gly
1               5                   10                  15

Gly Thr Glu Gly Gly Gly
            20

<210> SEQ ID NO 16
<211> LENGTH: 22
<212> TYPE: PRT
```

```
<213> ORGANISM: Artificial Sequence
<220> FEATURE:
<223> OTHER INFORMATION: Synthetic peptide

<400> SEQUENCE: 16

Ala Gly Gln Lys Glu Cys Lys Phe Gly Tyr Pro His Cys Leu Pro Trp
1               5                   10                  15

Gly Thr Glu Gly Gly Gly
            20

<210> SEQ ID NO 17
<211> LENGTH: 22
<212> TYPE: PRT
<213> ORGANISM: Artificial Sequence
<220> FEATURE:
<223> OTHER INFORMATION: Synthetic peptide

<400> SEQUENCE: 17

Ala Gly Ser Asp Trp Cys Gly Thr Trp Asn Asn Pro Cys Phe His Gln
1               5                   10                  15

Gly Thr Glu Gly Gly Gly
            20

<210> SEQ ID NO 18
<211> LENGTH: 26
<212> TYPE: PRT
<213> ORGANISM: Artificial Sequence
<220> FEATURE:
<223> OTHER INFORMATION: Synthetic peptide

<400> SEQUENCE: 18

Gly Asp Arg Leu His Cys Lys Pro Gln Arg Gln Ser Pro Trp Met Lys
1               5                   10                  15

Cys Gln His Leu Asp Pro Glu Gly Gly Gly
            20                  25

<210> SEQ ID NO 19
<211> LENGTH: 32
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 19

Asp Xaa Ala Cys Gly Asp Leu His Ala Cys Arg Pro Val Arg Gly Asp
1               5                   10                  15

Pro Trp Trp Ala Cys Thr Leu Gly Asp Pro Glu Gly Gly Gly Asn His
            20                  25                  30

<210> SEQ ID NO 20
<211> LENGTH: 26
<212> TYPE: PRT
<213> ORGANISM: Artificial Sequence
<220> FEATURE:
<223> OTHER INFORMATION: Synthetic peptide

<400> SEQUENCE: 20

Gly Asp Arg Tyr Leu Cys Leu Pro Gln Arg Asp Lys Pro Trp Lys Phe
1               5                   10                  15

Cys Asn Trp Phe Asp Pro Glu Gly Gly Gly
            20                  25
```

```
<210> SEQ ID NO 21
<211> LENGTH: 26
<212> TYPE: PRT
<213> ORGANISM: Artificial Sequence
<220> FEATURE:
<223> OTHER INFORMATION: Synthetic peptide

<400> SEQUENCE: 21

Gly Asp Tyr Ser His Cys Ser Pro Leu Arg Tyr Tyr Pro Trp Trp Lys
1               5                   10                  15

Cys Thr Tyr Pro Asp Pro Glu Gly Gly Gly
            20                  25

<210> SEQ ID NO 22
<211> LENGTH: 26
<212> TYPE: PRT
<213> ORGANISM: Artificial Sequence
<220> FEATURE:
<223> OTHER INFORMATION: Synthetic peptide

<400> SEQUENCE: 22

Gly Asp Gly Phe Thr Cys Ser Pro Ile Arg Met Phe Pro Trp Phe Arg
1               5                   10                  15

Cys Asp Leu Gly Asp Pro Glu Gly Gly Gly
            20                  25

<210> SEQ ID NO 23
<211> LENGTH: 26
<212> TYPE: PRT
<213> ORGANISM: Artificial Sequence
<220> FEATURE:
<223> OTHER INFORMATION: Synthetic peptide

<400> SEQUENCE: 23

Gly Asp Phe Ser Pro Cys Lys Ala Leu Arg His Ser Pro Trp Trp Val
1               5                   10                  15

Cys Pro Ser Gly Asp Pro Glu Gly Gly Gly
            20                  25
```